(12) United States Patent
Dawoud et al.

(10) Patent No.: US 10,959,618 B2
(45) Date of Patent: Mar. 30, 2021

(54) IMAGING TOOLBOX FOR GUIDING CARDIAC RESYNCHRONIZATION THERAPY IMPLANTATION FROM PATIENT-SPECIFIC IMAGING AND BODY SURFACE POTENTIAL MAPPING DATA

(71) Applicant: THE JOHNS HOPKINS UNIVERSITY, Baltimore, MD (US)

(72) Inventors: Fady Dawoud, Baltimore, MD (US); Karl H. Schuleri, Baltimore, MD (US); Amir Pourmorteza, Baltimore, MD (US); Albert C. Lardo, Baldwin, MD (US); Elliot McVeigh, Timonium, MD (US)

(73) Assignee: The Johns Hopkins University, Baltimore, MD (US)

( * ) Notice: Subject to any disclaimer, the term of this patent is extended or adjusted under 35 U.S.C. 154(b) by 752 days.

(21) Appl. No.: 15/310,580

(22) PCT Filed: May 12, 2015

(86) PCT No.: PCT/US2015/030279
§ 371 (c)(1),
(2) Date: Nov. 11, 2016

(87) PCT Pub. No.: WO2015/175469
PCT Pub. Date: Nov. 19, 2015

(65) Prior Publication Data
US 2017/0071675 A1    Mar. 16, 2017

Related U.S. Application Data

(60) Provisional application No. 61/991,941, filed on May 12, 2014.

(51) Int. Cl.
*A61B 5/00* (2006.01)
*A61B 6/00* (2006.01)
(Continued)

(52) U.S. Cl.
CPC .......... *A61B 5/0035* (2013.01); *A61B 5/0452* (2013.01); *A61B 5/0536* (2013.01);
(Continued)

(58) Field of Classification Search
None
See application file for complete search history.

(56) References Cited

U.S. PATENT DOCUMENTS 5,341,811 A * 8/1994 Cano .................... A61B 5/0428
600/508
7,587,074 B2 * 9/2009 Zarkh ....................... G06T 7/20
382/107
(Continued)

FOREIGN PATENT DOCUMENTS

WO        2013040546 A1    3/2013
WO        2013056082 A1    4/2013
WO    WO 2013/056082      *  4/2013

*Primary Examiner* — Katherine L Fernandez
(74) *Attorney, Agent, or Firm* — Harrity & Harrity, LLP

(57) ABSTRACT

The present invention is directed to a method for combining assessment of different factors of dyssynchrony into a comprehensive, non-invasive toolbox for treating patients with a CRT therapy device. The toolbox provides high spatial resolution, enabling assessment of regional function, as well as enabling derivation of global metrics to improve patient response and selection for CRT therapy. The method allows for quantitative assessment and estimation of mechanical contraction patterns, tissue viability, and venous anatomy from CT scans combined with electrical activation patterns from Body Surface Potential Mapping (BSPM). This multi-modal method is therefore capable of integrating electrical, mechanical, and structural information about cardiac structure and function in order to guide lead placement of CRT therapy devices. The method generates regional electro-mechanical properties overlaid with cardiac venous distribution and scar tissue. The fusion algorithm for combining (Continued)

all of the data suggests cardiac segments and routes for implantation of epicardial pacing leads.

20 Claims, 21 Drawing Sheets

(51) Int. Cl.
A61B 6/03 (2006.01)
A61B 34/10 (2016.01)
A61B 5/0452 (2006.01)
A61B 5/0536 (2021.01)
A61N 1/05 (2006.01)
A61N 1/362 (2006.01)
A61B 5/0408 (2006.01)

(52) U.S. Cl.
CPC ............ A61B 5/7203 (2013.01); A61B 5/743 (2013.01); A61B 6/032 (2013.01); A61B 6/4417 (2013.01); A61B 6/503 (2013.01); A61B 6/5247 (2013.01); A61B 34/10 (2016.02); A61N 1/0587 (2013.01); A61N 1/3627 (2013.01); A61B 5/04085 (2013.01); A61B 6/5217 (2013.01); A61B 2576/023 (2013.01)

(56) References Cited

U.S. PATENT DOCUMENTS

| 8,145,306 | B2 | 3/2012 | Lessmeier et al. |
| 2005/0096523 | A1* | 5/2005 | Vass ........................ A61B 6/032 600/407 |
| 2013/0072790 | A1* | 3/2013 | Ludwig .................. A61B 6/503 600/425 |
| 2013/0245473 | A1* | 9/2013 | Ramanathan ........ A61B 5/4848 600/509 |
| 2014/0023256 | A1* | 1/2014 | Nazarian .............. A61B 5/7203 382/131 |
| 2014/0088943 | A1 | 3/2014 | Trayanova et al. |
| 2015/0032014 | A1* | 1/2015 | Ghosh .................. A61B 5/4836 600/510 |
| 2015/0042646 | A1* | 2/2015 | Comaniciu ............. G06T 17/20 345/420 |

* cited by examiner

IMAGING TOOLBOX FOR GUIDING CARDIAC RESYNCHRONIZATION THERAPY IMPLANTATION FROM PATIENT-SPECIFIC IMAGING AND BODY SURFACE POTENTIAL MAPPING DATA

CROSS-REFERENCE TO RELATED APPLICATIONS

This application is a 35 U.S.C. § 371 U.S. national entry of International Application PCT/US2015/030279, having an international filing date of May 12, 2015, which claims the benefit of U.S. Provisional Application No. 61/991,941, filed May 12, 2014, the content of each of the aforementioned applications is herein incorporated by reference in their entirety.

GOVERNMENT LICENSE RIGHTS

This invention was made with government support under NIH R21 EB015638 awarded by the National Institutes of Health (NIH). The government has certain rights in the invention.

FIELD OF THE INVENTION

The present invention relates generally to medical imaging. More particularly, the present invention relates to a system and method for guiding cardiac resynchronization using computed tomography and body surface potential mapping.

BACKGROUND OF THE INVENTION

Heart failure is a major public health problem in the United States. Approximately 5 million people are affected, and an increasing number of hospitalizations and deaths are attributed to this disease. Biventricular (Biv) pacing delivered during cardiac resynchronization therapy (CRT) has emerged as a meaningful non-pharmacological therapy for patients with moderate to severe heart failure and left bundle branch block (LBBB). CRT has been shown in a number of large randomized clinical trials to improve clinical status as well as slow down or reverse left-ventricular (LV) remodeling that occurs as a result of the progression of heart failure in selected patients. However, the non-response rate among patients who receive CRT devices remains high, in a range of 30% to 40%. Among the factors that have been hypothesized to contribute to the high patient non-response rate to CRT therapy include mechanical dyssynchrony, electrical dyssynchrony, scar burden, and LV pacing lead location. Approaches to address these factors in patients receiving CRT devices include looking at one component of dyssynchrony separately (i.e. mechanical only, electrical only, scar only), using low-resolution imaging techniques (i.e. a handful of body surface leads, echocardiography, nuclear SPECT/PET) or invasive methods (i.e. catheters).

It would therefore be advantageous to provide a comprehensive, non-invasive imaging strategy for characterizing each of these factors to better optimize and personalize delivery of the therapy.

SUMMARY OF THE INVENTION

The foregoing needs are met by the present invention which provides a method for optimizing cardiac resynchronization therapy (CRT) including using an electrical imaging module to collect electrical image data regarding heart function. The method includes performing calculations using the electrical image data to determine electrical-based heart metrics. The method also includes using a mechanical imaging module to collect mechanical image data regarding heart function and performing calculations using the mechanical image data to determine mechanical-based heart metrics. Additionally, the method includes combining the electrical-based and mechanical-based metrics using spatial and temporal registration techniques to select target regions for CRT.

In accordance with an aspect of the present invention, the method includes executing the method using a non-transitory computer readable medium. The method also includes collecting the electrical image data using body surface potential mapping and collecting the mechanical image data using computed tomography scanning. The method includes using electrical metrics taking the form of at least one selected from a group consisting of electrical reconstruction and electrical dyssynchrony. Electrical dyssynchrony can be calculated using normalized inter-ventricular QRS integral, mean total activation, normalized inter ventricular QRS integral dispersion, dispersion of LV activation, change in QRST integral, and uniformity of electrical activation to determine electrical dyssynchrony. The method includes using mechanical metrics taking the form of at least one selected from a group consisting of regional mechanical function analysis, Stretch Quantifier Endocardial Engraved Zones (SQUEEZ), electromechanical delay, and venous and scar modules.

In accordance with still another aspect of the present invention, a system for optimizing cardiac resynchronization therapy (CRT) includes an electrical imaging module configured to collect electrical image data regarding heart function. The system includes a mechanical imaging module configured to collect mechanical image data regarding heart function. Additionally, the system includes a non-transitory computer readable medium configured for executing steps, wherein the steps include receiving the electrical image data and receiving the mechanical image data. The system includes performing calculations using the electrical image data to determine electrical-based heart metrics, performing calculations using the mechanical image data to determine mechanical-based heart metrics, and combining the electrical-based and mechanical-based metrics using spatial and temporal registration techniques to generate a visual output for selecting target regions for CRT.

In accordance with yet another aspect of the present invention, the system includes the electrical imaging module being configured for body surface potential mapping, and the mechanical imaging module being configured for computed tomography scanning. The mechanical imaging module takes the form of a computed tomography scanner. The non-transitory computer readable medium is configured for using electrical metrics taking the form of at least one selected from a group consisting of electrical reconstruction and electrical dyssynchrony. The system can use one of normalized inter-ventricular QRS integral, mean total activation, normalized inter ventricular QRS integral dispersion, dispersion of LV activation, change in QRST integral, and uniformity of electrical activation to determine electrical dyssynchrony. The non-transitory computer readable medium is further configured for using mechanical metrics taking the form of at least one selected from a group consisting of regional mechanical function analysis, regional mechanical function analysis, Stretch quantifier of endocardial engraved zones (SQUEEZ), electromechanical delay, and venous and scar modules. The electrical imaging module includes surface electrodes.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and.

DETAILED DESCRIPTION

Figure 1:
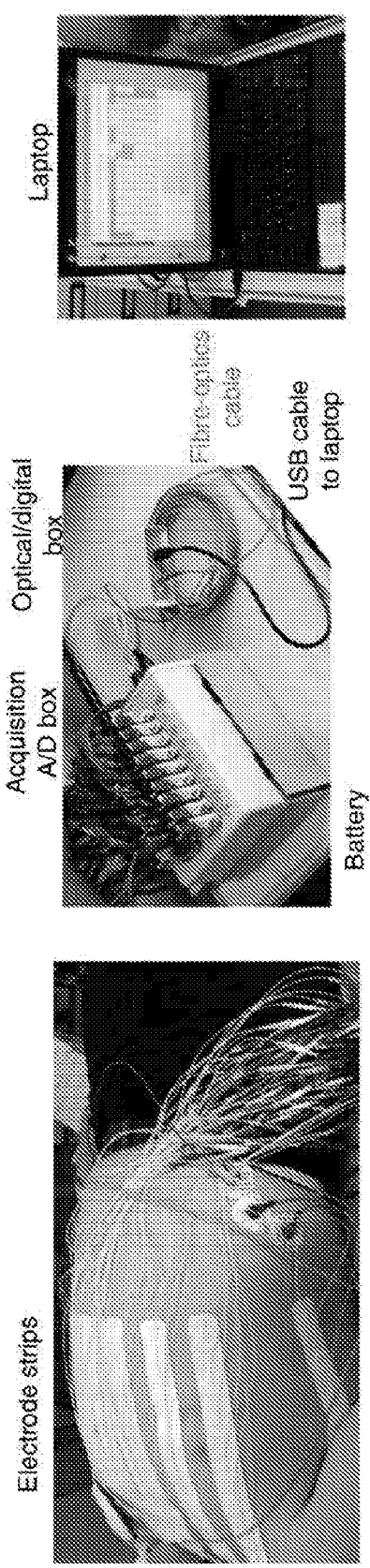
FIG. 1 illustrates images of a body surface potential mapping setup according to an embodiment of the present invention.

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains, having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The present invention is directed to a method for combining assessment of different factors of dyssynchrony into a comprehensive, non-invasive toolbox for treating patients with a CRT therapy device. The toolbox provides high spatial resolution, enabling assessment of regional function, as well as deriving global metrics to improve patient response and selection for CRT therapy. The method further allows for quantitative assessment and estimation of mechanical contraction patterns, tissue viability, and venous anatomy from CT scans combined with electrical activation patterns from Body Surface Potential Mapping (BSPM). BSPM can be acquired non-invasively, during routine scans. This multi-modal method is therefore capable of integrating electrical, mechanical, and structural information about cardiac structure and function in order to guide lead placement of CRT therapy devices. The method also generates regional electro-mechanical properties overlaid with cardiac venous distribution and scar tissue. The fusion algorithm for combining all of the data also suggests cardiac segments and routes for implantation of epicardial pacing leads.

A number of factors are thought to contribute in part or in whole to non-responsiveness to CRT therapy. These contributory factors include, but are not limited to, mechanical dyssynchrony, electrical dyssynchrony, scar substrate, venous anatomy, and left ventricle pacing location. The method described herein allows for the integration of information obtained non-invasively from standard CT and ECG mapping exams. These CT and ECG mapping exams can be performed prior to CRT device implantation, to allow for planning and guiding the procedure rapidly, on-site with minimal user input.

A method according to the present invention includes collecting electrical and mechanical data related to a subject's heart function, in order to make determinations regarding CRT device implantation. Many acquisition procedures can be used for obtaining both the electrical and mechanical data, and these acquisition procedures will be discussed further herein. However, the acquisition procedures discussed herein should not be considered limiting, and any electrical and/or mechanical data acquisition procedure suitable for use with the present invention can be used.

An electrical imaging acquisition module according to the method of the present invention can take the form of one or more of the following acquisition procedures and processing steps. Data collected from the acquisition methods can be processed using optimization method (Tikhonov regularization), beat-to-beat averaging to improve signal to noise ratio, arrangement of body surface electrodes to yield efficient capture of body surface ECGs, and 3D to 2D projection of activation maps and design of CT acquisition protocol for electrode labeling. As noted above, the procedures detailed herein are not meant to be considered limiting and any other suitable procedures could also be used.

One such electrical acquisition procedure is body-surface potential mapping (BSPM). BSPM records electrocardiograms (ECG) at numerous locations in order to capture the complete time-varying electrical activity of the heart on the torso. Surface electrodes are placed on the torso and connected via cables to a multi-channel acquisition system to record body potentials during various electrophysiological conditions (sinus rhythm and device biventricular pacing). The exact locations of the heart with respect to the electrodes is obtained from computed tomography imaging. The acquisition system by way of example, can in some embodiments provide band-pass filtering, signal amplification, multiplexing and digitization of all channels simultaneously at over 1 kHz sampling frequency and over 16-bit digitization resolution. The acquisition system is optically isolated from the subject outputs and connects to a computing device, such as a laptop computer, running a program written on a non-transitory computer readable medium. The program allows for visual display and data storage. Recordings are performed for less than a minute and then stored for subsequent analysis. These exemplary embodiments are in no way meant to be considered limiting. Computational routines are used to process the acquired BSPM data. The data is digitally filtered (for example, low-pass 100 Hz, high-pass 0.25 Hz and notch 60 Hz) in two directions to produce zero-phase shift. However, any suitable filtering scheme can be used. Faulty leads due to poor skin-electrode contact, motion artifact or inaccessibility of the torso area are estimated using a least-squares interpolation method. Dynamic beat-averaging is performed to improve signal-to-noise ratio. The data from the BSPM can then be used to create several models of heart function, described herein. The examples of the models of heart function are not meant to be considered limiting.

Electrical Reconstruction Model:

Potential distributions on the epicardial surface of the heart are estimated non-invasively using electrical BSPM measurements. The potential distribution in the conductive torso is modeled using Laplace's equation. Subject-specific discretized geometries of the heart's epicardial ventricles and body surface are related with respect to electrical potentials ($V_B$ and $V_H$) using a linear forward transformation (A) according to $$V_B = A^* V_H \tag{1}$$

The inverse problem which reconstructs epicardial potential electrograms (EGM) is ill-posed and small errors in the input BSPM measurements, inevitable in practical settings, generates unbound error in the solution. Inverse epicardial potential ($V_H$) are calculated using Tikhonov regularization with the regularization parameter (t) controlling the degree of smoothing according to the minimization problem $$\min \|A^* V_H - V_B\|^2 + t^* \|V_H\|^2 \tag{2}$$

The singular value decomposition (SVD) is used to decompose the matrix A according to $$\text{SVD}(A) = U \Sigma Y^T$$

where U and Y is orthonormal basis of row space and column space, respectively, and Σ is singular values diagonal matrix. The inverse solution is obtained by selecting the regularization parameter (t) such that a trade-off is achieved between accuracy (residual error in Eqn. 2) and stability (solution semi-norm). Epicardial potentials at each time instant are computed successively for the whole duration of the heart beat and displayed on the heart geometry for analysis. Solution of the minimization function for $V_H$ is $$V_H(t) = \sum_{i=1}^{k} (u_i \cdot V_B) y_i + \sum_{i=k+1}^{n} \frac{\mu_i}{\mu_i^2 + t^2} (u_i \cdot V_B) y_i, \tag{3}$$

where (p) is the singular values of the SVD of transfer matrix (A), ($u_i$) are columns of the orthonormal matrix U and V is the columns space basis matrix. Direct formula for the reconstructed epicardial potential ($V_H$) is $$\Phi_H = (A^T A + \lambda I)^{-1} A^T \Phi_B \tag{4}$$

Figure 2:
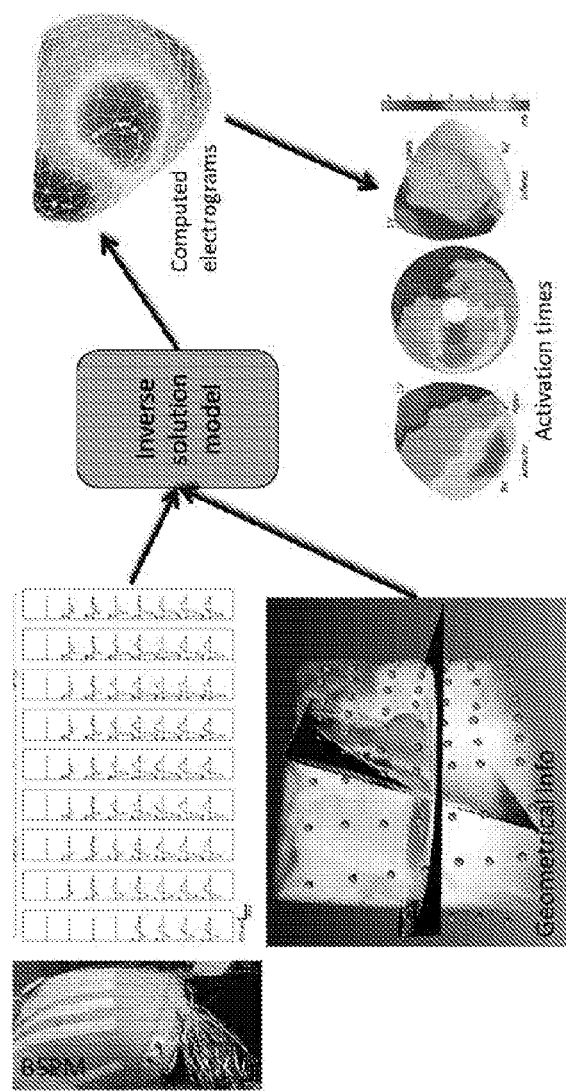
FIG. 2 illustrates a diagram of an electrical imaging module methodology according to an embodiment of the present invention.
Figure 3:
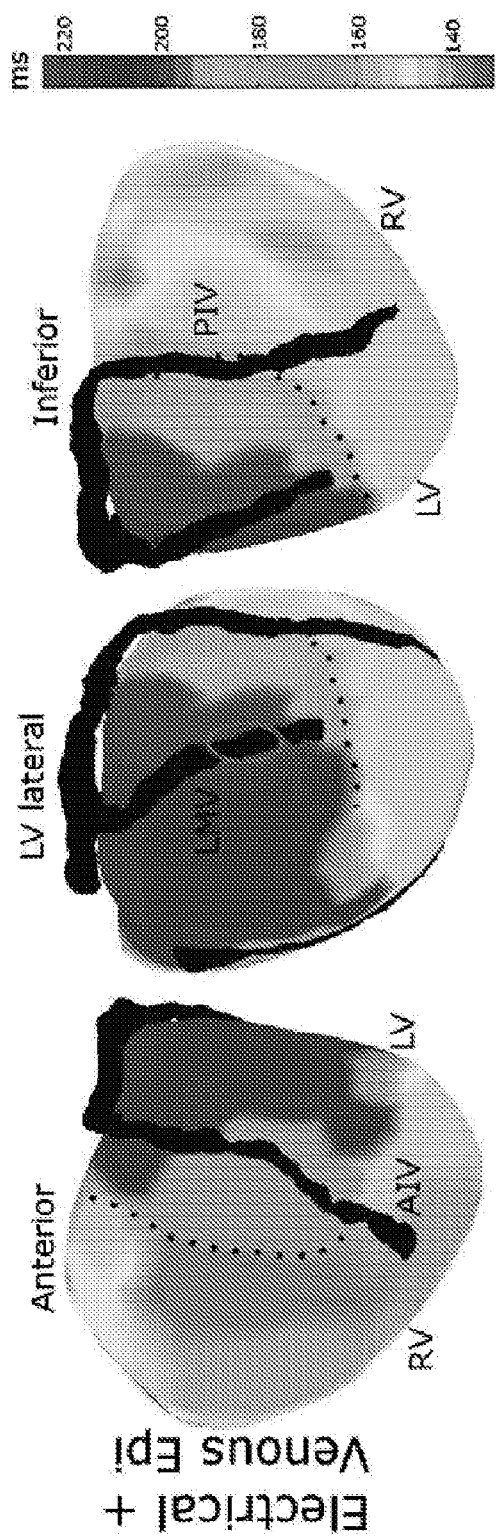
FIG. 3 illustrates a visual representation of a reconstructed electrical activation, according to an embodiment of the present invention.

FIGS. 1 and 2 illustrate images of an exemplary recording setup and a diagram of flow of data/analysis steps to reconstructed epicardial electrograms, respectively. From the reconstructed epicardial electrograms, activation times are computed from the point of steepest downward slope as is conventional in contact unipolar mapping. A finite difference method is used to estimate first derivatives, as illustrated in the reconstructed electrical activation images illustrated in FIG. 3.

Electrical Dyssynchrony Metrics:

A number of regional and global metrics leveraging the capability of imaging local electrical activation have been developed to characterize the extent of electrical dyssynchrony. These metrics have been tested on human and animal datasets to establish normal and abnormal range of values for electrical dyssynchrony.

Normalized Inter-ventricular QRS integral (ΔQRSi) is the inter-ventricular difference between average right ventricular (RV) and left ventricular (LV) regional integral of the QRS complex over the first one-third of the QRS duration normalized to the range ±1 by the absolute maximum QRS integral according to:

$$\text{Regional } QRSi = \frac{\int_0^{QRSd/3} \Phi(t) dt}{\max \int_0^{QRSd/3} \Phi(t) dt} \Delta QRSi = \sum_{i \in RV} QRSi - \sum_{i \in LV} QRSi$$

The rationale behind using the QRS integral stems from the fact that as the depolarization wave breaks through the epicardial wall and starts travelling away, the local electrogram exhibits an early negative (Q-wave) deflection while epicardial regions that activate later exhibit a positive followed by a negative deflection (RS-wave). By taking the integral of regional inverse electrograms over the first one third of the QRS interval, the extent and timing of depolarization is captured such that an early steep Q-wave indicating earlier and faster activation will have a negative QRS integral. On the other hand, an RS wave indicating a later activation will have a positive QRS integral. This global dyssynchrony index (ΔQRSi) was shown to be capable of quantifying the electrical changes that accompany CRT therapy with minimal variation over multiple consecutive beats. A clear threshold of 0.05 was capable of classifying paced from the non-paced rhythms with 100% sensitivity.

Mean total activation (ΔMTA) is the inter-ventricular difference between average right ventricular (RV) and left ventricular (LV) regional activation times (computed as the point of steepest negative slope) according to $$\text{Regional } \tau = \min dV_H/dt \Delta MTA = \Sigma_{i \in RV}\tau - \Sigma_{i \in LV}$$

This index measures the inter-ventricular delay of conduction between the right and left ventricles.

Normalized Inter-ventricular QRS integral dispersion (QRSi-SD) is intra-ventricular standard deviation of the normalized regional QRS integral (used in ΔQRSi) over the epicardial LV.

Dispersion of LV activation (LV-SD) is the intra-ventricular standard deviation of the regional activation times over the epicardial LV.

ΔQRST-Integral is the intra-ventricular difference between average right ventricular (RV) and left ventricular (LV) regional integral of the complete QRS, ST-segment and T-wave complexes.

Uniformity electrical activation (E-CURE) is the intra-ventricular synchronous activation of the epicardial LV computed as $$\sum \frac{S_0}{S_0 + S_1}$$

where $S_0$ and $S_1$ are zero and first Fourier transform components of the reconstructed electrogram voltage versus short axis angle over the whole ventricles.

A mechanical imaging acquisition module according to the method of the present invention can take the form of CT imaging: Standard CT imaging protocol is performed with ECG monitoring using a multi-detector scanner. A heart rate of <100 beats/min is achieved using beta-blocker medication. After scout acquisition and slice prescription, a bolus of contrast agent is injected intravenously. An image of coronary veins is acquired 1 min post contrast using a low-dose coronary angiogram acquisition. Dynamic cardiac function and delayed-enhancement images are acquired at first pass, 1-min and 7.5 mins after contrast delivery to capture mechanical contraction as well as scar regions and venous anatomy. Image acquisition is performed under breath hold maneuvers. Raw data are reconstructed as contiguous equal slice thickness. Cardiac function images are later reconstructed at increments of the R-R interval. Radiation dose can be minimized by using dose-modulation methods and iterative reconstruction techniques. An exemplary dose of radiation is on the order of 4-8 mS. However, any other suitable dose of radiation can also be used.

The data from CT images can then be used to create models of heart function, described herein. While CT is given as an example herein, these examples are not meant to be considered limiting. Therefore, any other suitable imaging modality could also be used.

Figure 4A:
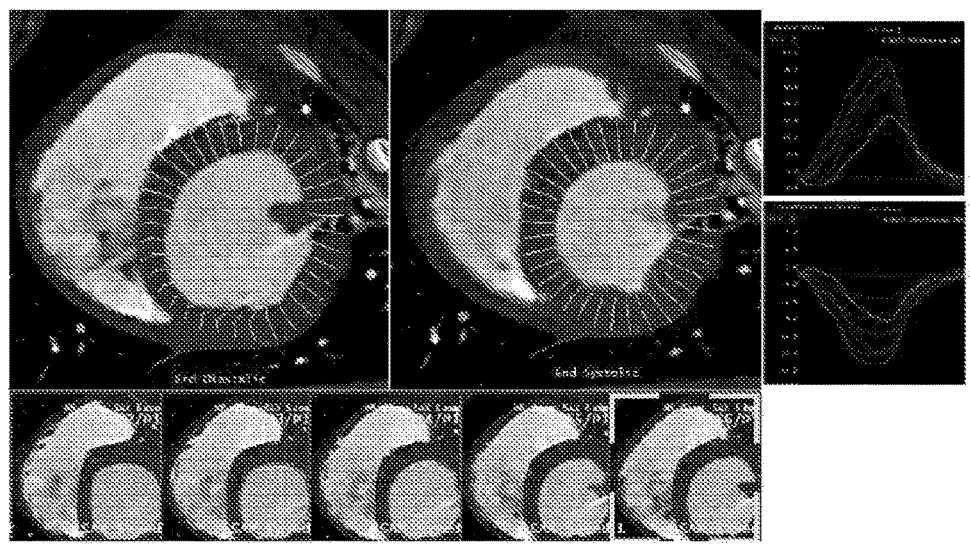
FIG. 4A illustrates an MTT interface showing end-diastole/end-systole tracking of the endo- and epi-cardial borders as well as radial/circumferential strain curves.
Figure 4B:
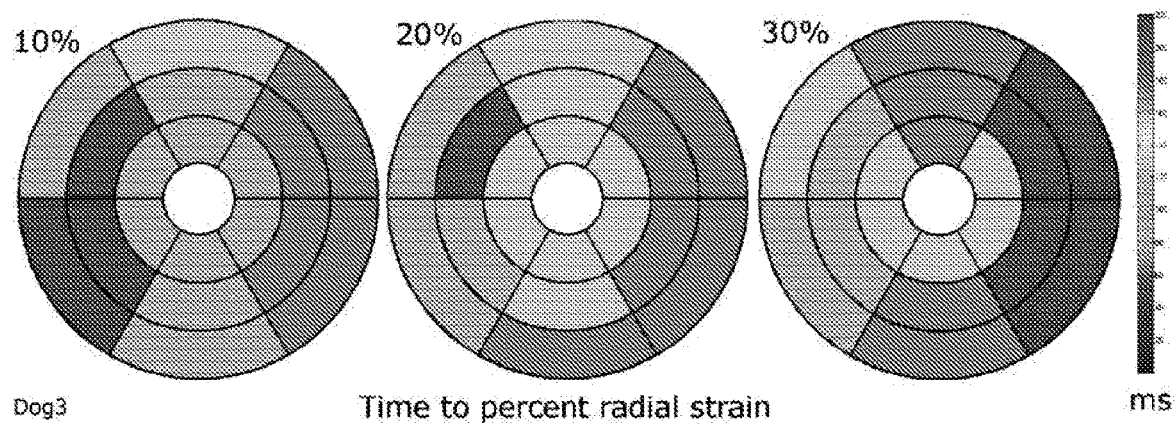
FIG. 4B illustrates time to 10%, 20% and 30% peak radial strain projected on 17-segment bullseye plot.

Regional Mechanical Function Analysis (MTT):

A program written on a non-transitory computer readable medium is used to contour endo-cardial and epicardial borders in re-sliced cine SA images. The program calculates angle-independent motion vectors of multiple tracking points between consecutive frames by assigning a square template image (10×10 mm) around each tracking point and then searching in the next frame within a search field for the best matching pixel pattern. The program package has been validated comparing CT-computed radial strain to MR-tagging derived radial strain. Radial and circumferential strain are calculated from endo-, mid- and epi-cardial tracking points. Time plots of regional strain were used to mark local mechanical activation times as time to peak strain (tpk) and time to some % of peak contraction (for example time to 10% peak activation, t10%). FIGS. 4A and 4B illustrate the non-transitory software interface and computed mechanical activation times. FIG. 4A illustrates an MTT interface showing end-diastole/end-systole tracking of the endo- and epi-cardial borders as well as radial/circumferential strain curves. FIG. 4B illustrates time to 10%, 20% and 30% peak radial strain projected on 17-segment bullseye plot.

Figures 5A, 5B, 5C, 5D:
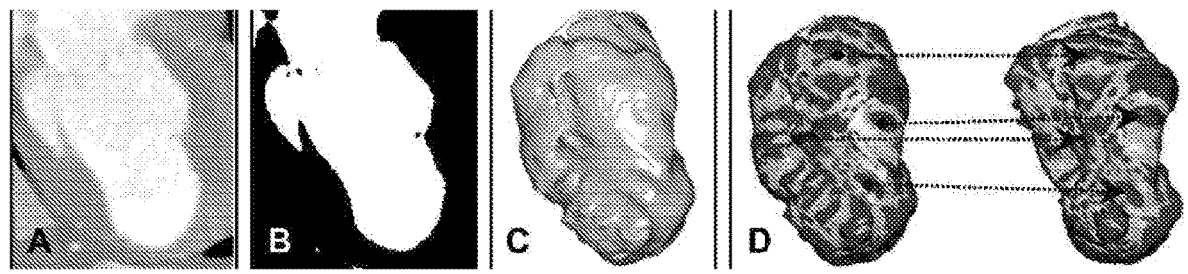
FIGS. 5A-5E illustrate images representing steps for calculating SQUEEZ.
Figure 5E:
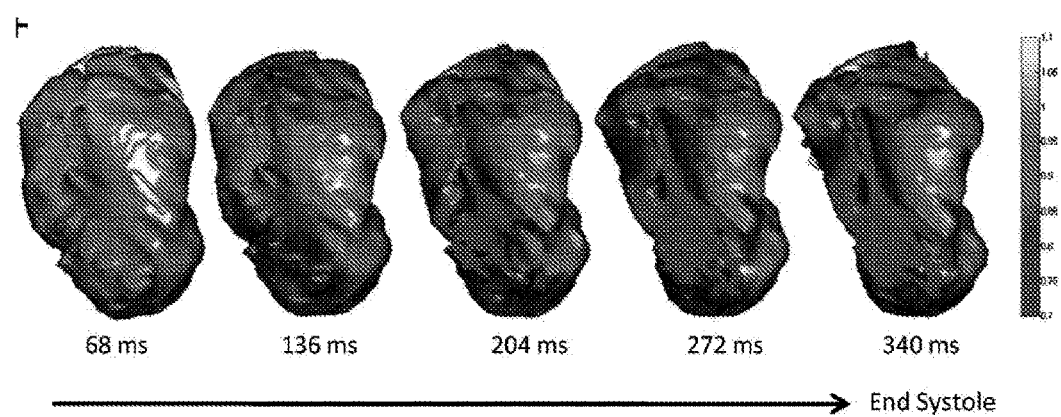
Figure 6A:
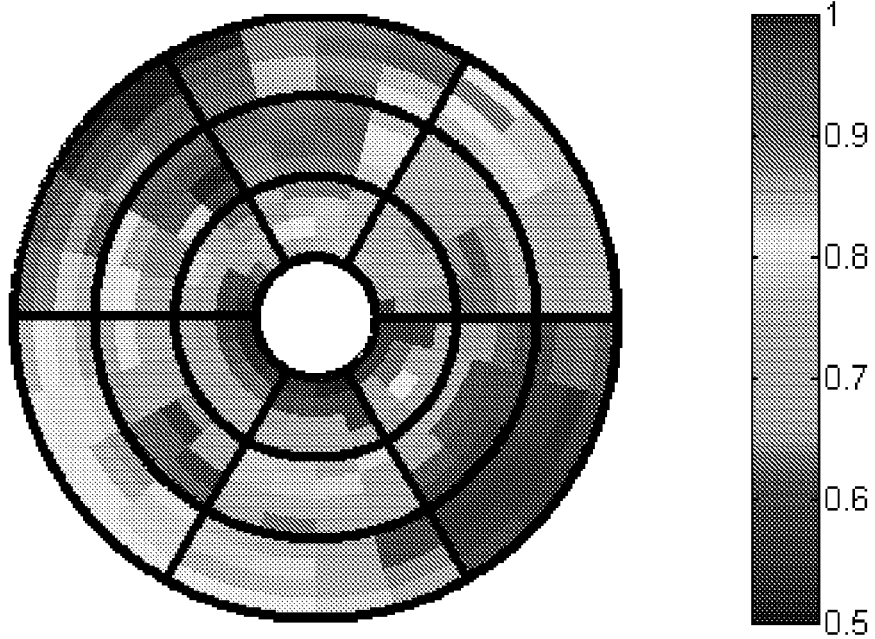
FIGS. 6A and 6B illustrate a graphical view of a bullseye polar plot of SQUEEZ values at end systole.
Figure 6B:
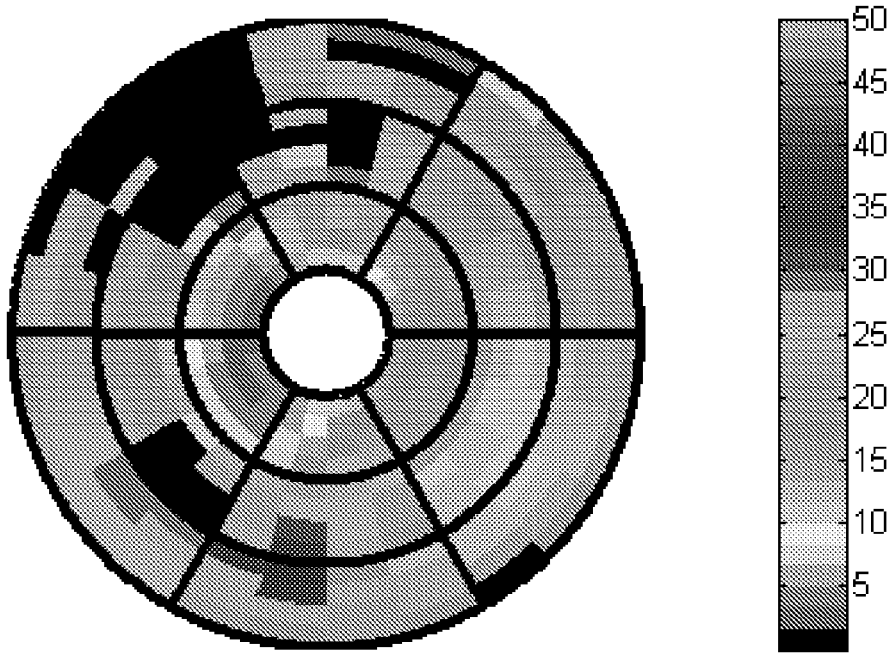

Regional Mechanical Function Analysis (SQUEEZ):

Stretch quantifier of endocardial engraved zones (SQUEEZ) is used to track the LV wall motion by segmenting the blood from myocardium and calculating trajectories of the fine trabecular endocardial features seen on the blood cast. FIGS. 5A-5E illustrate images representing steps for calculating SQUEEZ. FIGS. 5A-5C illustrate blood pool volume segmented from the CT scan volume by threshholding. FIG. 5D illustrates an image of a shape index value calculated to encode features engraved by the trabecular structures on the endocardial surface. FIG. 5E illustrates an image showing that SQUEEZ maps are calculated on the endocardial surface at five cardiac phases from end diastole to end systole. Activation times can be derived from the strain versus time plots defined by time to 10% and to peak activation. FIGS. 6A and 6B illustrate a graphical view of a bullseye polar plot of SQUEEZ values at end systole (FIG. 6A) and % time to a 10% of peak activation. The black represents kinetic segments defined as peak strain <0.1. SQUEEZ-CURE: A mechanical dyssynchrony metric based on the Fourier transform of the SQUEEZ values versus circumferential angel is applied to characterize the extent of discoordinated contraction of the left ventricle.

Figure 7A:
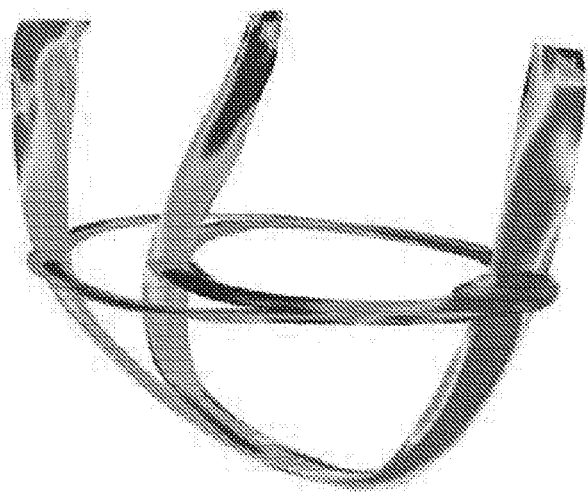
FIGS. 7A and 7B illustrates images of the 3D distribution of EMD in a simulation study and computed by the imaging toolbox.
Figure 7B:
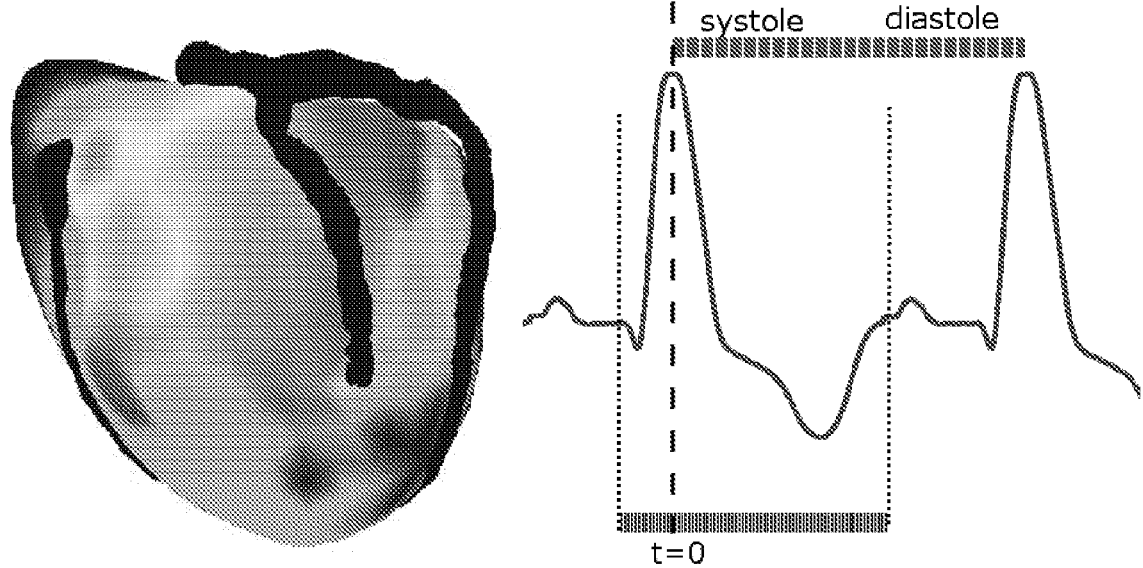

Electromechanical Delay (EMD Module):

FIGS. 7A and 7B illustrate images of the 3D distribution of EMD in a simulation study and computed by the imaging toolbox. Regional electrical activation times are computed from reconstructed electrograms at the point of steepest down slope. Mechanical activation times are computed from regional SQUEEZ profiles or MTT strain profiles at time point of 10% peak contraction. Both measurements are normalized relative to the peak of the R-wave in lead II and then subtracted to compute regional EMD variation map.

Figure 8:
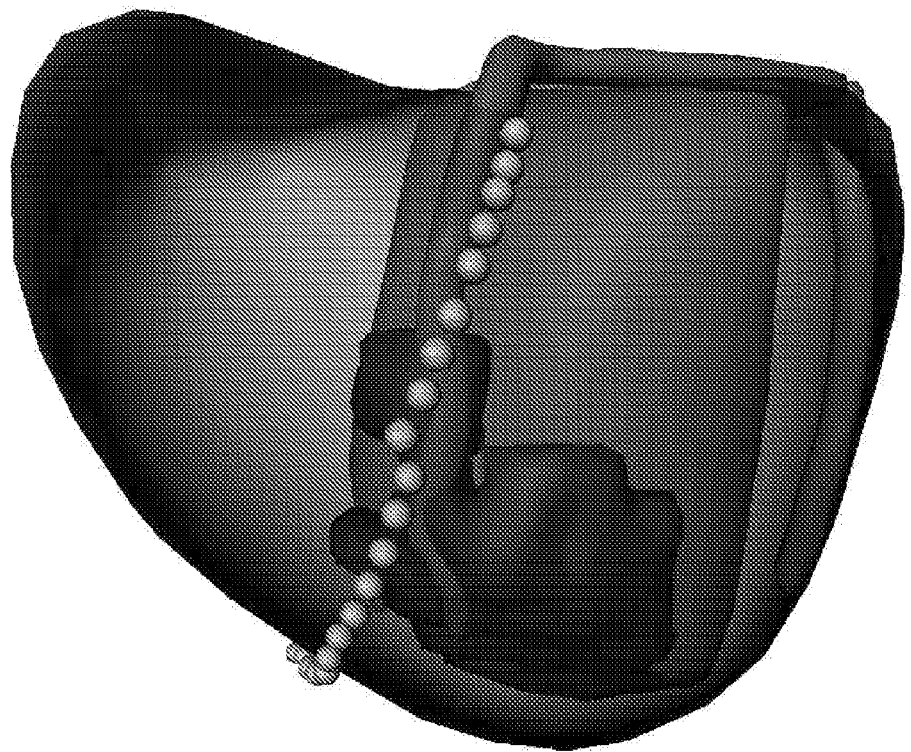
FIG. 8 illustrates images of segmented scar and venous anatomy obtained from the 1-min and 7.5 min delayed enhancement images, respectively.

Venous and Scar Modules:

Delayed enhancement CT acquisition protocol is used to capture the venous anatomy and scar distribution with minimal radiation dose through the use of prospective gating and iterative reconstruction methods. FIG. 8 illustrates images of segmented scar and venous anatomy obtained from the 1-min and 7.5 min delayed enhancement images, respectively.

Other Electro-Mechanical Dyssynchrony Metrics:

EMDV (Electro-mechanical dyssynchrony vector): We propose to use a Euclidean-based index to characterize the extent of electrical and mechanical dyssynchrony defined as $\sqrt{CURE \cdot E^2 + CURE \cdot M^2}$ where CURE·M and CURE·E are the Fourier-based metric used earlier. Based on how important mechanical versus electrical dyssynchrony we can further use a weighted Euclidean coefficients ($K_E$ and $K_M$) according to $\sqrt{K_E*CURE \cdot E^2 + K_M*CURE \cdot M^2}$. This index in the vector form shows the extent of both electrical and mechanical dyssynchrony seperately while the magnitude of it shows the magnitude of the combined effect of both factors.

E/M CURE ratio: ratio of CURE electrical (E-CURE) to CURE mechanical (SQUEEZ-CURE) can be used to reflect degree of dyssyhncrony the closer to 1 the less dyssynchrony and the closer to 0 the more dyssynchrony.

Mechanical Model (such as SQUEEZ-CURE)+any electrical model/metric: The mechanical dyssynchrony index based on a mechanical model such as SQUEEZ can be combined with any of the previously mentioned electrical dyssynchrony models/metrics (ΔQRSi, ΔQRSi, LV-SD and ΔQRST-Integral) using, for example, a ratio of the mechanical dyssynchrony to the electrical dyssynchrony or a Euclidean distance calculation using the mechanical dyssynchrony and the elec after proper normalization to indicate the combined effect of any of these factors. Combining the mechanical with the electrical requires spatial and temporal registration techniques. Rigid registration is used to align the anatomical data to minimize the least-squared error between image-segmented mechanical and electrical geometries. Temporal alignment of electrical and mechanical modalities is performed by normalizing the activation times with respect to the heart rate and offsetting time origin to the peak of the R-wave in a body surface electrocardiographic (EKG) lead.

Figure 9:
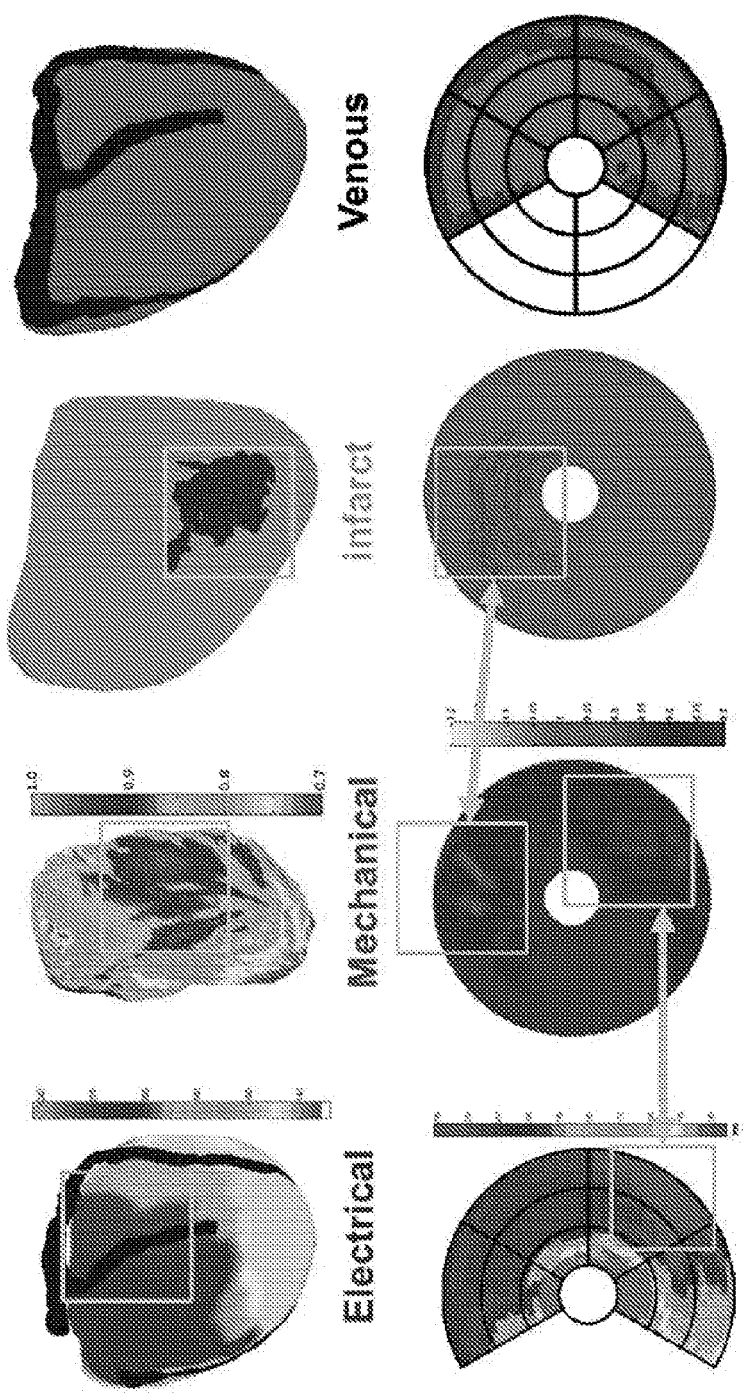
FIG. 9 illustrates images of multimodal imaging of venous, infarct, mechanical and electrical maps.

Multi-Modality Image Fusion:

Both epicardial and endocardial data are re-sampled in the short axis orientation at equal slice thickness and displayed on the standard AHA bull's-eye polar plot to facilitate cross-modality comparisons. FIG. 9 illustrates images of multimodal imaging of venous, infarct, mechanical and electrical maps. Midwall anterior infarct corresponding to the anterior area of depressed mechanical contraction. Area of latest electrical activation on the basal inferolateral region corresponds to the another area of impaired mechanical contraction.

Figure 10:
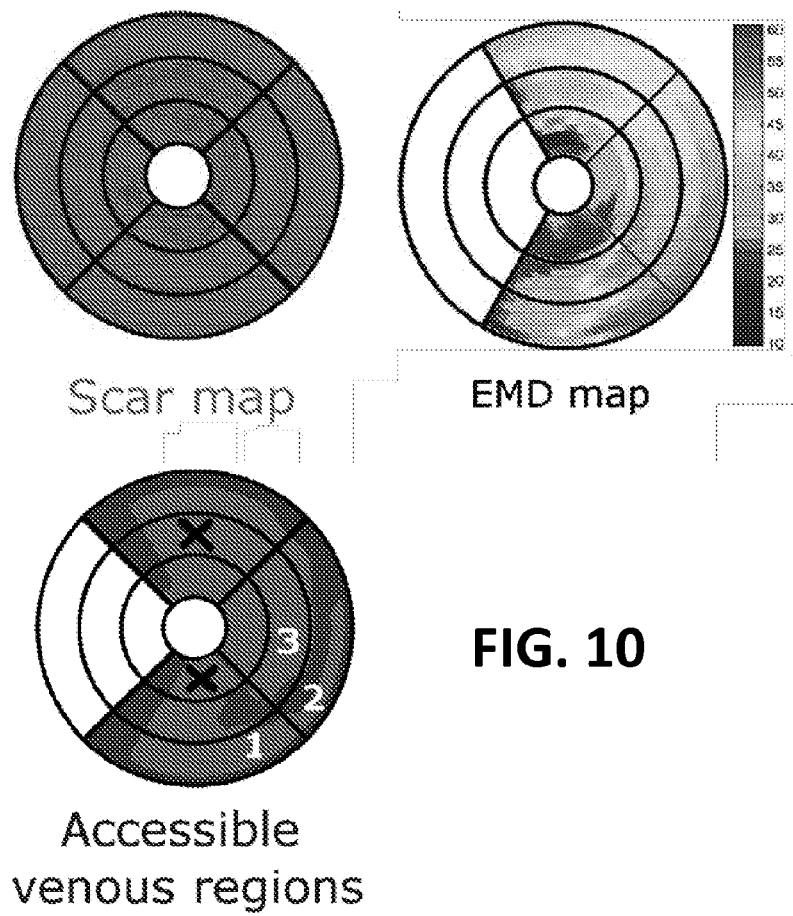
FIG. 10 illustrates an exemplary display for the software tool, user interface showing a scar map, an EMD map, and accessible venous regions.

Lead Implantation Planning:

Software tool developed perform the following sequential functions to guide lead placement in the image guided group. FIG. 10 illustrates an exemplary display for the software tool, user interface showing a scar map, an EMD map, and accessible venous regions. The user interface and program on the non-transitory computer readable medium will also do the following: 1) display and exclude myocardial segments with CT derived scar >50%, 2) in remaining qualifying segments, compute an electrical and mechanical activation difference (EMD) map and then display the three segments with the least electromechanical delay as optimal segments, 4) display the coronary vein anatomy derived from CT to determine the vein that will provide the easiest access to the optimal pacing location segments. Lead placement is guided by calculating the time difference between onset of electrical to onset of mechanical activation (electromechanical delay).

It should be noted that the models and metrics described herein can be executed with a program(s) fixed on one or more non-transitory computer readable medium. The non-transitory computer readable medium can be loaded onto a computing device, server, imaging device processor, smartphone, tablet, phablet, or any other suitable device known to or conceivable by one of skill in the art. It should also be noted that herein the steps of the method described can be carried out using a computer, non-transitory computer readable medium, or alternately a computing device, microprocessor, or other computer type device independent of or incorporated with an imaging or signal collection device. Indeed, any suitable method of calculation known to or conceivable by one of skill in the art could be used. It should also be noted that while specific equations are detailed herein, variations on these equations can also be derived, and this application includes any such equation known to or conceivable by one of skill in the art. A non-transitory computer readable medium is understood to mean any article of manufacture that can be read by a computer. Such non-transitory computer readable media includes, but is not limited to, magnetic media, such as a floppy disk, flexible disk, hard disk, reel-to-reel tape, cartridge tape, cassette tape or cards, optical media such as CD-ROM, writable compact disc, magneto-optical media in disc, tape or card form, and paper media, such as punched cards and paper tape.

The following describes an exemplary implementation. The exemplary implementation is in no way considered to be limiting, and the present invention can be implemented in any way described above or known to or conceivable by one of skill in the art.

In summary, ischemic DHF was induced in 6 dogs using coronary occlusion, left-bundle ablation and tachy RV pacing. Full body ECG was recorded during native rhythm followed by volumetric first-pass and delayed enhancement CT. Regional electrical activation were computed and overlaid with segmented venous anatomy and scar regions. Reconstructed electrical activation maps show consistency with LBBB point-by-point mapping starting on the RV and spreading in a "U-shaped" pattern to the LV. Lines of slow conduction are seen parallel to anterior or inferior interventricular grooves. Mechanical contraction shows large septal to lateral delay (80±38 vs 123±31 ms, p=0.0001) with lateral wall showing larger passive early pre-stretch (−0.88±0.69 vs −0.23±0.41, p=0.0001). Prolonged EMD regions are quantified mainly on the inferior or posterior LV as predicted by whole-heart simulations with inter-subject variability possibly related to scar location and electromechanical activation. This exemplary implementation shows that CT in combination with ECGI to image electromechanical substrates in ischemic DHF can provide valuable regional information to facilitate pre-procedure planning of CRT.

More particularly, a validated novel heart failure canine model combing myocardial infarct (MI), LBBB and rapid pacing, mimicking resembling ischemic dyssynchronous CHF in humans, was adopted for the study. All animal studies were approved by the Johns Hopkins University Institutional Animal Care and Use Committee. Experiments were performed on 6 adult mongrel dogs weighing 23±1.5 kg (Telazol-Ketamine-Xylazine cocktail for anesthesia induction and 2% Isoflurane gas for maintenance). MI was created by engaging the left anterior descending (LAD N=4) or left circumflex (LCx N=2) coronary arteries under fluoroscopic guidance as described previously. Coronary vessels were occluded for 180 mins then animals underwent left-bundle radiofrequency ablation within 1 week and later implanted with a pacemaker programmed for rapid right-atrial pacing (120 bpm) for 4-5 weeks to amplify progression into heart failure.

Body surface potential mapping (BSPM) and computed tomography (CT) were performed on the same day, 55±14 days after MI. Ex-vivo magnetic resonance MRI (ex-vivo MR) was performed for gold standard assessment of tissue viability.

Body Surface Potential Mapping: Briefly, 120 disposable radiolucent Ag/AgCl surface electrodes were placed in a specific arrangement on the torso and were connected via cables to a multi-channel acquisition system (Active Two, BioSemi, Amsterdam, Netherlands) to record body surface electrocardiograms (ECG) to a laptop computer running a custom acquisition program (MAPPER, Dalhousie University, Halifax, NS, Canada).

Figures 11A, 11B, 11C, 11D:
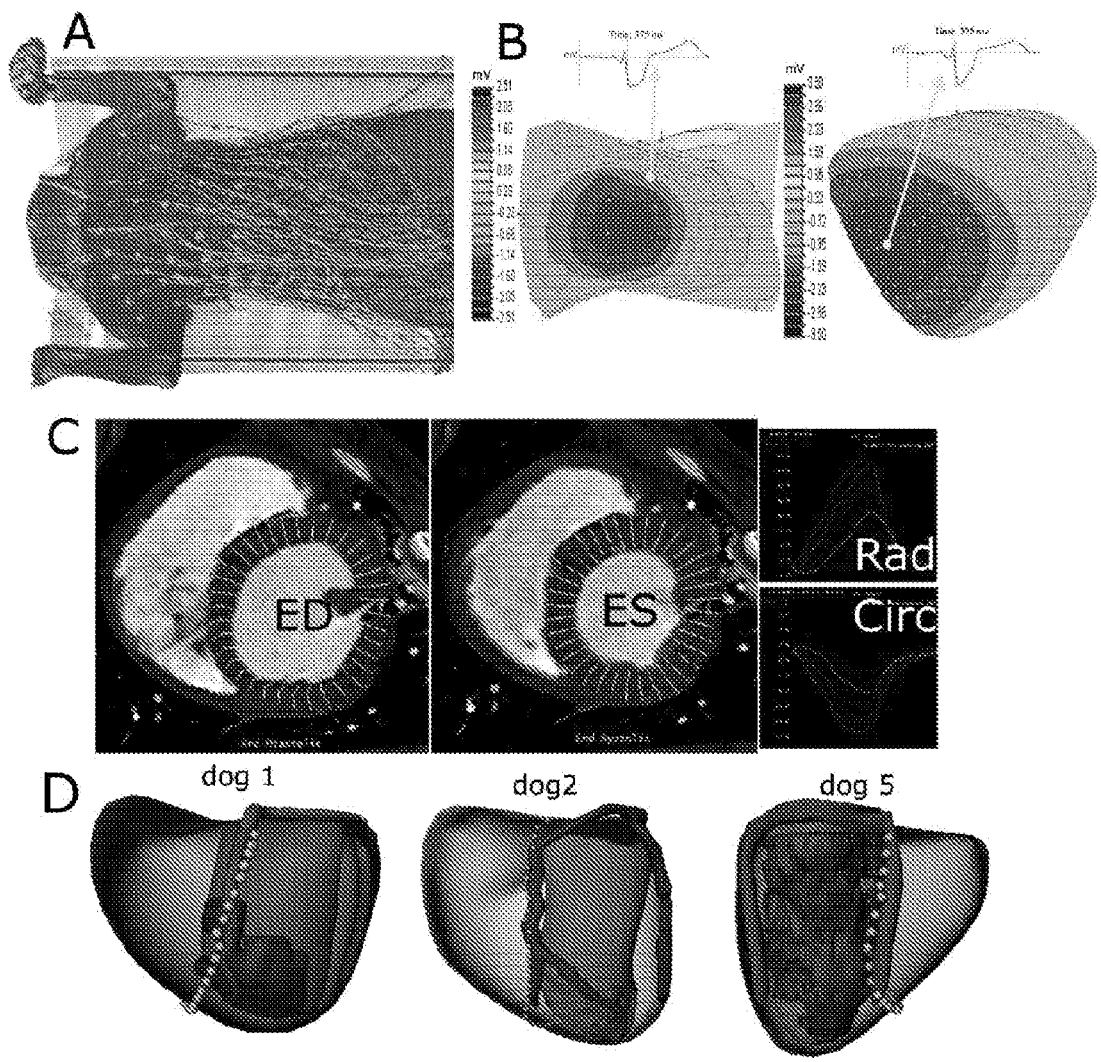
FIGS. 11A-11D illustrate electrical, mechanical and anatomical imaging components.

Computed Tomography: Animals were scanned with ECG-gating and suspended respiration using a 0.5-mm 320-detector scanner (Aquilion 320, Toshiba, Japan). Imaging was performed during first pass post injection of a 100-mL bolus of iodixanol using retrospectively-gated cardiac function assessment (CFA) protocol with the following parameters: gantry rotation time 275 ms, temporal resolution approximately 50 ms, detector collimation 0.5 mm×320, helical pitch variable depending on heart rate, tube voltage 120 kV and tube current 400 mA. The scan was manually triggered (~1 min post) to achieve a good opacification of the LV chamber as well as coronary veins. Delayed-enhancement CT (DECT) images were acquired 7 minutes after contrast delivery when it was found to best capture wash out of contrast from scar. An ultra-low dose thoracic helical scan was performed to capture the location of body surface electrodes relative to the heart, as illustrated in FIG. 11A.

Electrocardiographic Imaging (ECGI): Epicardial electrograms (EGM) were reconstructed non-invasively from electrical BSPM measurements using a boundary element model of body and heart geometries, as illustrated in FIG. 11B. Electrode labeling, surface segmentation and discretization were performed using commercial software (Amira™ 4.1, Mercury Computer Systems, Chelmsford, Mass.). The reconstruction inverse problem was solved using Tikhonov regularization (zero-order and L-curve methods). Custom MATLAB™ computational routines were used to process ECG's and reconstruct inverse EGM's. Electrical activation times (telect) were computed as the point of steepest downward slope. Three-dimensional (3D) electrical activation maps were re-sampled in the short-axis direction to obtain 2D AHA polar maps.

Electrical Dyssynchrony Metrics: Four global metrics derived from reconstructed EGM's were computed to quantify electrical dyssynchrony. Two inter-ventricular: normalized integral of early EGM depolarization (ΔQRSi) and average chamber activation (ΔMTA). Two Intra-LV: LV standard deviation of activation (LV-SD) and LV activation range (LVAT).

Regional Myocardial Function CT Analysis: Dynamic CFA images were reconstructed from raw data at 5% increments of the R-R interval with 0.5-mm slice thickness and oblique re-slicing was done to obtain 5-mm slice thickness LV short-axis slices. Commercial software (Myocardial Tissue Tracking, MTT, Toshiba, Japan) was used to contour endocardial and epicardial borders in short-axis images. The software calculates angle-independent motion vectors of multiple tracking points between consecutive frames by assigning a square template image (10×10 mm) around each tracking point and searching in the next frame for the best matching pixel pattern. The software package has been validated comparing CT-computed radial strain to MR-tagging derived radial strain. Radial strain computed from endocardial tracking points was used for mechanical analysis. Time plots of regional strain were used to mark local mechanical activation from time to 10% of peak contraction (tm10% pk) and time to peak contraction (tmpk). FIG. 11C shows an example of the software interface and the computed regional radial and circumferential strain profiles. Pre-stretch regions that undergo passive early stretch (due to contraction of opposing wall) were quantified from early negative strain peaks preceding main positive contraction.

Mechanical Dyssynchrony Metrics: The circumferential and radial uniformity (CURE and RURE) indices were applied to strain-derived data to characterize global mechanical dyssynchrony (perfect synchronous contraction yields a value of 1 while completely dyssynchronous contractions yields zero).

Scar Quantification and Data Fusion: In-vivo DECT images were analyzed to delineate infarct size and location (image intensity >3 standard deviation from remote healthy myocardium). Ex-vivo delayed enhancement MR images were also analyzed to provide a gold standard assessment of tissue viability. ECGI and CT mechanical maps were acquired in the same modality and did not require registration. Anatomical landmarks (anterior/inferior interventricular grooves and LV long-axis) were used to properly divide and re-sample 3D geometries All geometries were re-sampled in the short axis orientation at 5-mm slice thickness and for displayed on the standard AHA plot to facilitate cross-technique and cross-animal comparisons. FIG. 11D shows representative examples of the segmented epicardial, endocardial, venous and scar structures.

FIGS. 11A-11D illustrate electrical, mechanical and anatomical imaging components. FIG. 11A illustrates a volume-rendered image of animal body surface electrodes and wires. FIG. 11B illustrates processed body potential maps and reconstructed epicardial potential map during early depolarization. FIG. 11C illustrates image-based myocardial tissue tracking (MTT) of the endo- and epicardial borders at end-diastole (ED)/end-systole (ES) as well as automatically computed radial (Rad)/circumferential (Circ) strain profiles. D: Image fusion of venous anatomy (blue), scar (gray), LV epicardial and endocardial surfaces for dogs 1, 2 and 5.

Figure 12:
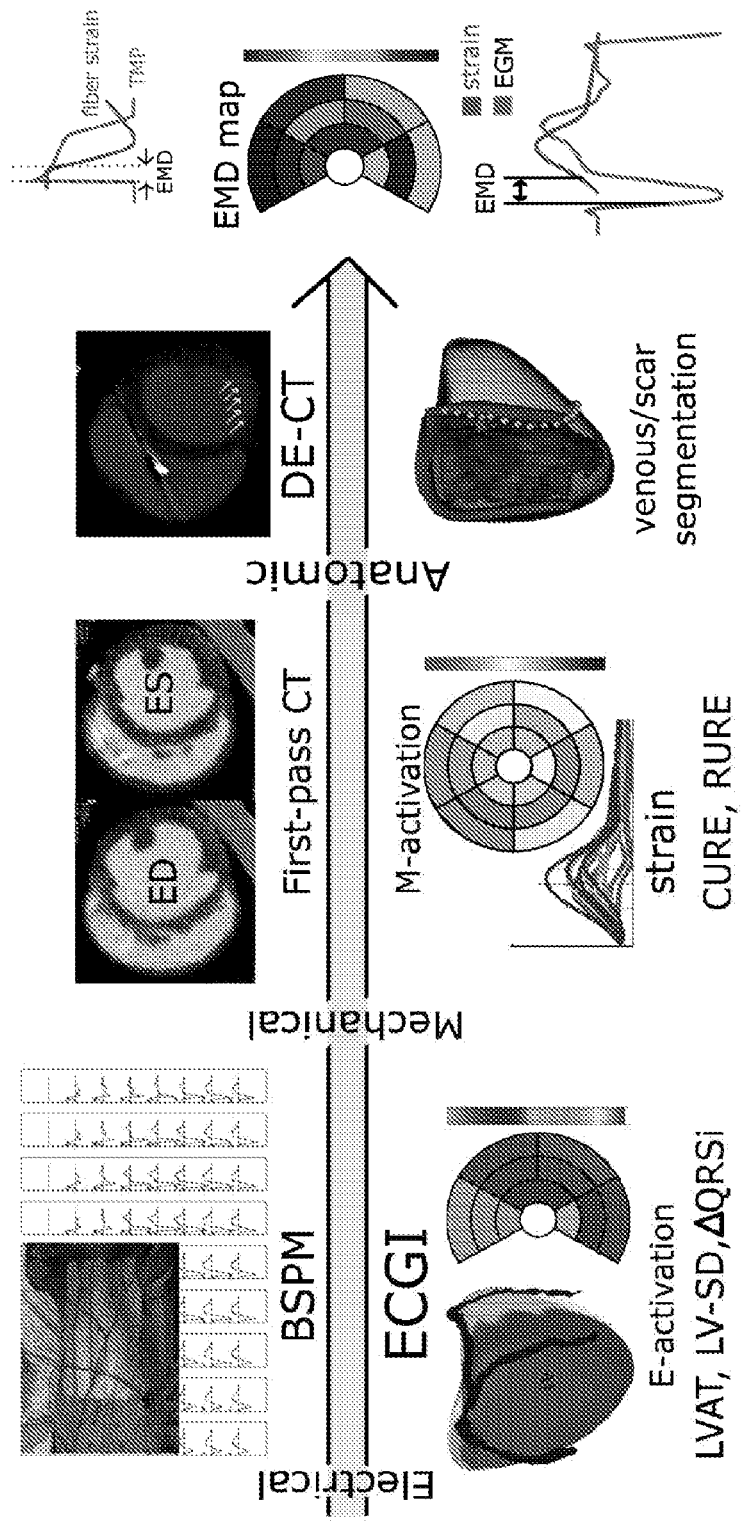
FIG. 12 illustrates an overview schematic of the imaging toolbox, BSPM records electrical information, CT captures mechanical function, scar location (from DECT) and venous anatomy, and ECGI reconstructs electrical activation (E-activation) from BSPM data and body/heart geometries.

Electro-mechanical Delay (EMD) Analysis: Regional EMD values per AHA segment were computed by subtracting regional mechanical activation (10%-to-peak contraction, t10% pk) from regional electrical activation times (telect after offsetting in time relative to R-wave peak and normalizing by the RR interval). FIG. 12 summarizes all components (electrical, mechanical and anatomical) of the imaging toolbox. FIG. 12 illustrates an overview schematic of the imaging toolbox, BSPM records electrical information, CT captures mechanical function, scar location (from DECT) and venous anatomy, and ECGI reconstructs electrical activation (E-activation) from BSPM data and body/heart geometries. First pass CT images are contoured to obtain regional strain profiles and mechanical activation (M-activation). Electro-mechanical delay (EMD) maps time difference of mechanical (strain) and electrical (EGM) activation times over AHA regions similar to cellular-level EMD (time from transmembrane potential, TMP, upstroke to onset of fiber shortening). Global electrical and mechanical dyssynchrony metrics are derived from regional information (more details in the results section)

Continuous variables were represented as mean±standard deviation. Pearson test was performed to test for correlation. For comparison of mean values between two groups, two-tailed Student's t-test was used. P-value of 0.05 was considered statistically significant. All analyses were performed with SPSS statistical package (SPSS, Inc., Chicago, Ill.).

Six dogs underwent the CT/ECGI/ex-vivo MR imaging protocol. Global baseline characteristics at the imaging time point are summarized in Table 1, below. Table 1 shows animal baseline characteristics: MI, myocardial infarction, HR, heart rate at imaging point, M/F, male/female, LV, left ventricle, LVEF, LV ejection fraction, LVEDV, LV end-diastolic volume, LVESV, LV end-systolic volume, DECT, delayed-enhancement CT.

TABLE 1

|  | LAD (N = 4) | LCx (N = 2) | All |
|---|---|---|---|
| Gender | 2M 1F | 0M 2F | 2M 4F |
| MI age (days) | 47 ± 3 | 72 ± 13 | 55 ± 14 |
| HR (bpm) | 91 ± 32 | 72 ± 13 | 84 ± 27 |
| LVEF (%) | 28 ± 11 | 32 ± 3 | 30 ± 9 |
| LVEDV (mL) | 119 ± 21 | 87 ± 16 | 109 ± 24 |
| LVESV (mL) | 84 ± 5 | 59 ± 13 | 76 ± 14 |
| LV mass CT (g) | 75 ± 8 | 73 ± 10 | 74 ± 8 |
| LV mass ex-vivo MR (g) | 75 ± 8 | 73 ± 13 | 74 ± 9 |
| Infarct mass DECT (g) | 1.9 ± 0.7 | 4.4 ± 4.0 | 2.7 ± 2.3 |
| Infarct mass ex-vivo MR (g) | 2.2 ± 1.4 | 4.4 ± 2.7 | 2.9 ± 2.0 |

Figures 13A, 13B:
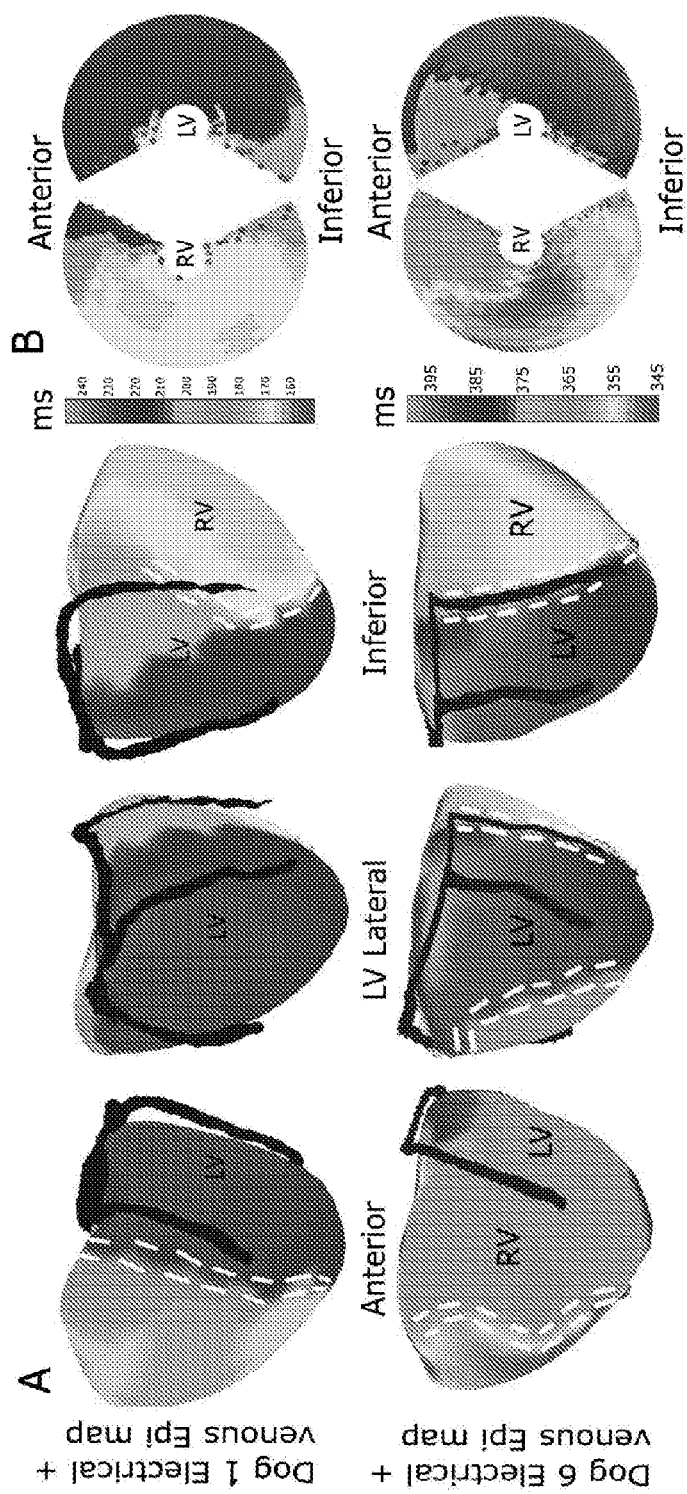
FIG. 13A illustrates a reconstructed electrical activation in dogs 1 and 6.
FIG. 13B illustrates AHA polar plots of epicardial electrical activation of both dogs displayed separately on the RV and LV.

Electrical Activation:

During sinus rhythm, activation maps showed a right-to-left direction of propagation (medium grey to dark grey, as illustrated in FIGS. 13A and 13B) consistent with a LBBB defect starting from the RV free wall and gradually spreading towards the LV lateral wall. Lines of slow conduction (>40 ms) were seen in all dogs and were generally oriented in the basal/apical direction frequently parallel or overlapping the anterior and posterior inter-ventricular grooves (FIGS. 13A and 13B—dashed white lines). These lines also seemed to appear generally around the periphery of infarcted regions. FIG. 3A shows an example of the 3D electrical activation for dog 1 (LAD infarct—top, 2 lines of block) and dog 6 (LAD/LCx infarct—bottom, 3 lines of block). The corresponding activation maps projected on the standardized AHA polar plot are shown in FIG. 13B. Table 2, below, summarizes electrophysiological parameters for all animals including QRSd, QRS duration, HR, heart rate, QTd, QT interval, ΔMTA, inter-ventricular mean total activation electrical dyssynchrony index, ΔQRSi, inter-ventricular normalized QRS integral of early electrical depolarization dyssynchrony index, LV-SD, intra-LV regional electrical activation standard deviation dyssynchrony index, LVAT, intra-LV range of regional electrical activation dyssynchrony index, telect, regional electrical activation time. ΔMTA and ΔQRSi global electrical dyssynchrony metrics indicated prolonged inter-ventricular delay (−22±5 and −0.30±0.13 ms, respectively) while intra-LV metrics LV-SD and LVAT showed prolonged LV activation (26±8 and 84±18 ms, respectively). The region that activates the latest did not vary greatly with location and size of scar and was contained mainly in the lateral basal segments.

TABLE 2

|  | LAD (N = 4) | LCx (N = 2) | All |
|---|---|---|---|
| Surface ECG | | | |
| QRSd (ms) | 105 ± 10 | 104 ± 40 | 104 ± 20 |
| QTd (ms) | 358 ± 86 | 410 ± 31 | 375 ± 73 |
| HR (bpm) | 90 ± 31 | 59 ± 4 | 80 ± 29 |
| Inter-ventricular | | | |
| ΔMTA (ms) | −22 ± 7 | −22 ± 1 | −22 ± 5 |
| ΔQRSi | −0.36 ± 0.12 | −0.19 ± 0.04 | −0.30 ± 0.13 |
| Intra-LV | | | |
| LV-SD (ms) | 28 ± 6 | 21 ± 11 | 26 ± 8 |
| LVAT (ms) | 88 ± 13 | 76 ± 30 | 84 ± 18 |
| Regional | | | |
| Latest $t_{elect}$ segment | 6, 6, 6, 5 | 6, 5 | 5 or 6 |

FIG. 13A illustrates a reconstructed electrical activation in dogs 1 and 6. Latest electrical activation appears basal infero-lateral for dog 6 and basal antero-lateral for dog 1. FIG. 13B illustrates AHA polar plots of epicardial electrical activation of both dogs displayed separately on the RV and LV.

Figures 14A, 14B, 14C:
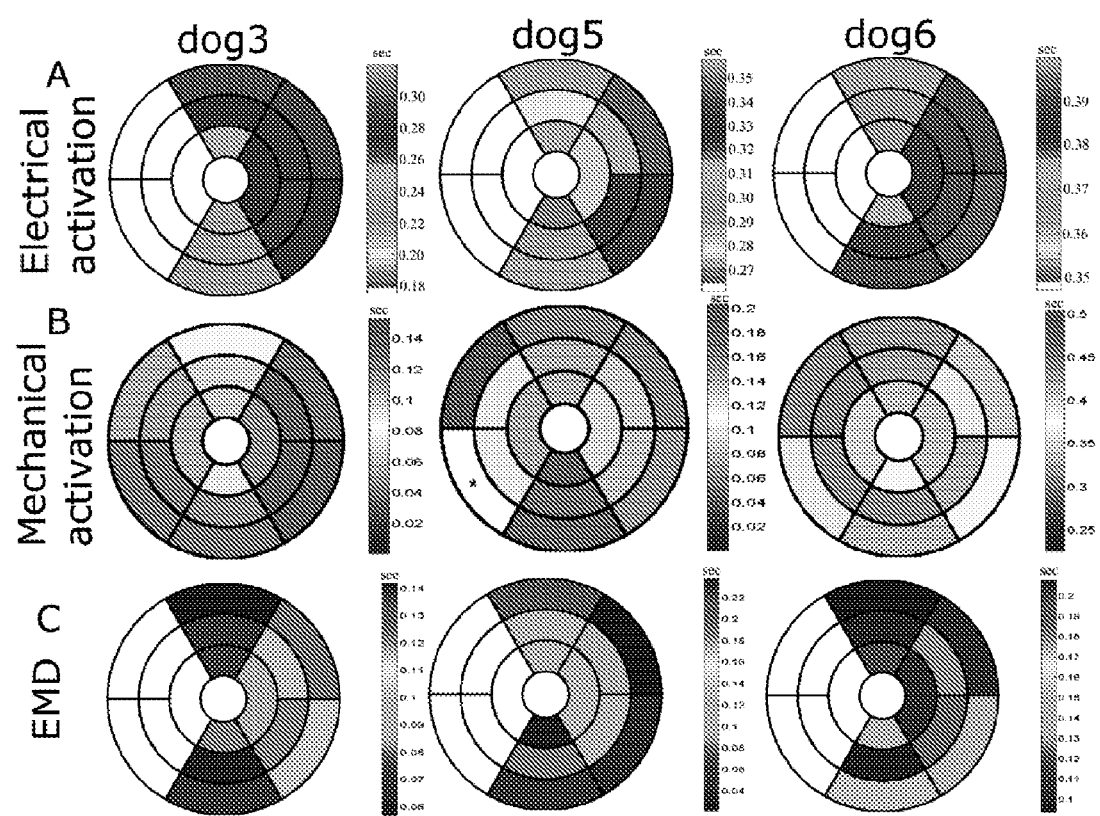
FIGS. 14A-14C illustrate electro-mechanical coupling.

Mechanical Activation: Mechanical activation times over the AHA segments were computed as the time-to-10%-peak radial endocardial strain (FIG. 14B). As expected, the activation sequence is generally directed from the septum to the lateral wall (tm10% pk 80±38 ms vs. 123±31 ms, p=0.0001). Also, LAD segments tended to activate later for LCx occlusion animals while LCx segments activated later for LAD occlusions animals although it did not reach statistical significance. Radial peak strain percentage in infarcted segments was significantly lower than healthy ones (49±23 vs 62±23, p=0.032) possibly indicating impaired thickening of these segments. CURE and RURE global mechanical dyssynchrony metrics showed depressed values (0.66±0.19 and 0.67±0.19, respectively) indicating dis-coordination of mechanical contraction (normal human subjects have CURE values of 0.96±0.01). FIGS. 14A-14C illustrate electro-mechanical coupling. FIG. 14A illustrates electrical activation averaged over AHA segments. All dogs show latest activation on the lateral LV wall. FIG. 14B illustrates time-to-10% peak radial endocardial strain from MTT. Dog 3 has general activation starting on the septum and spreading in both anterior and inferior direction with lateral wall activating the latest. Dog 6 shows clockwise activation with inferior wall activating the latest. FIG. 14C illustrates electro-mechanical delay maps show largest EMD regions coinciding with regions of latest mechanical delay in dogs 5 and 6 while discordant in dog 3 (lateral for mechanical vs inferior for EMD). Table 3, below, shows radial endocardial strain comparison between septal/lateral segments and scar/no scar segments including: Rad tmpk, time to peak radial strain, Rad tm10% pk, time to 10% peak radial strain, Rad pk, Radial strain peak percentage, Rad pre-stch pk, Radial strain pre-stretch peak percentage.

TABLE 3

|  | Septal (N = 30) | Lateral (N = 30) | p-value | No Scar (N = 78) | Scar (N = 18) | p-value |
|---|---|---|---|---|---|---|
| Rad $tm_{pk}$ (ms) | 340 ± 60 | 363 ± 51 | 0.145 | 352 ± 53 | 356 ± 58 | 0.81 |
| Rad $tm_{10\% pk}$ (ms) | 80 ± 38 | 123 ± 31 | 0.0001 | 105 ± 40 | 98 ± 48 | 0.525 |
| Rad pk (%) | 48 ± 23 | 68 ± 21 | 0.001 | 62 ± 23 | 49 ± 23 | 0.032 |
| Rad pre-stch pk (%) | −0.23 ± 0.41 | −0.88 ± 0.69 | 0.0001 | −0.55 ± 0.66 | −0.64 ± 0.51 | 0.575 |

Pre-Stretch:

Regional differences of amount of pre-stretch percentage were quantified in all animals. Radial pre-stretch strain peaks were smallest in septal segments increasing gradually in anterior/inferior segments and reaching highest amount on lateral segments in both basal and mid-wall levels. Late-activated lateral LV segments showed significantly higher radial thickening percentage compared to early-activated septal segments (−0.88±0.69 vs. −0.23±0.41, p=0.0001).

Electro-Mechanical Coupling and Delay:

Regional electromechanical delay over all segments was elevated (90±50 ms) compared to normal values of approximately between 40-80 ms reported in simulation and experimental studies. Electrical and mechanical regional activation maps showed heterogeneous electro-mechanical coupling. In dog 3, mechanical activation generally followed electrical activation with concordant regions of latest activation appearing on the lateral basal wall while in dog 5 maps showed discordant electro-mechanical coupling with latest electrical activation basal antero-lateral and latest mechanical activation mid-wall inferior (FIGS. 14A and 14B). In general, regions of increased EMD appeared either in the inferior or infero-lateral segments with largest delay segment varying over the long axis (FIG. 14C) except for dog 2 where largest EMD was apical antero-lateral (see supplementary material). The region of largest EMD coincided with regions of latest mechanical delay in 4 dogs, while it was discordant in 2 dogs (for example, lateral for mechanical versus inferior for EMD in dog 3, FIGS. 14A-14C).

Figures 15A, 15B, 15C, 15D, 15E:
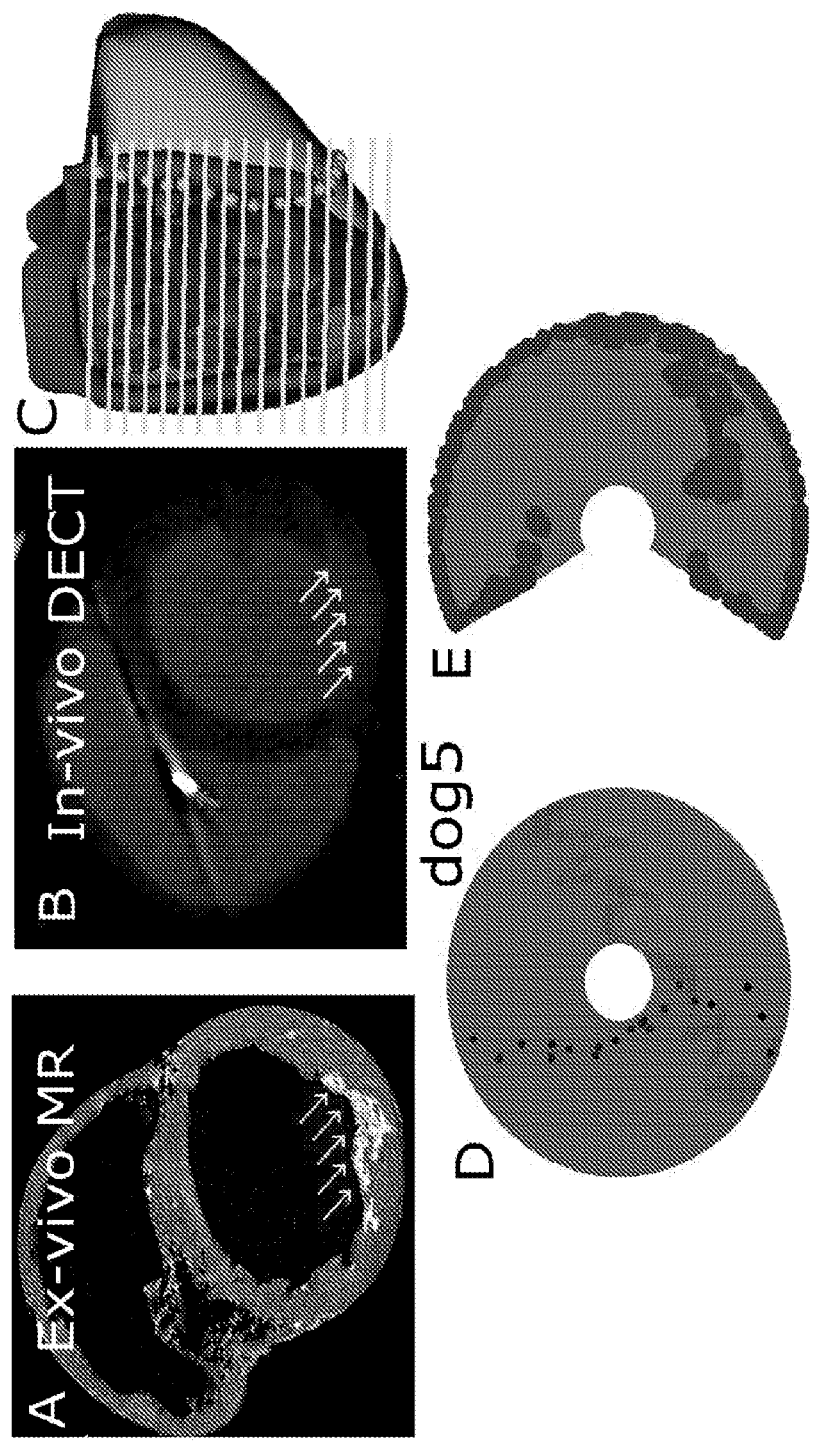
FIGS. 15A-15E show an example of LV scar seen in DECT images.

Venous Anatomy and DECT:

FIGS. 15A-15E show an example of LV scar seen in DECT images. Scar mass delineated by DECT (2.70±2.3 g) had significant correlation (R-Pearson 0.923, p=0.026) to scar mass analyzed by gold standard ex-vivo MR (2.90±2.0 g). Also, scar extent from both modalities overlaps closely when registered and visualized in 3D. A clear advantage of DECT as can be seen in FIG. 15B where good cardiac function images are obtained in spite of the presence of metal implants such as pacemakers/ICD devices and leads. The 3D anatomical structures were re-sampled in the short-axis direction (FIG. 15C yellow lines) to produce AHA polar plots of scar anatomy (FIG. 15D). venous anatomy (FIG. 15E) in order to facilitate guiding lead placement. FIGS. 15A-15E illustrate scar and venous anatomy distribution in dog 5. FIG. 15A is a mid-wall ex-vivo MR slice showing LCx scar (yellow arrows). FIG. 15B is an LCx infarct (yellow arrows) detected by DECT in the presence of a pacing lead (red arrow). FIG. 15C is a short-axis slicing of venous and scar structures to produce 2D polar projections. FIGS. 15D and 15E illustrate a surface extent of scar and venous tree projected on AHA polar plots.

In the exemplary implementation, feasibility and application of combining novel imaging techniques (function CT, DECT and ECGI) to characterize important functional and anatomical components attributed to the non-response of ischemic dyssynchronous heart failure hearts to CRT is demonstrated: namely, electrical activation, mechanical activation, venous anatomy and scar substrate. This is the first time non-invasive and personalized CT- and ECGI-derived information were acquired and synthesized to gain insight into the regional and global interplay among all these factors. It is shown in a clinically relevant canine model of myocardial infarction, LBBB and heart failure that this data can be obtained and used to deduce regional anatomical and functional properties useful for pre-planning of CRT epicardial lead placement. Furthermore, the present invention is directed to completely non-invasive and regional subject-specific distribution and quantification of electro-mechanical delay maps consistent with experimental and simulation studies. These maps show substantial variability, both regionally within an individual heart, and from one heart to another.

Electrical Function:

The sequence of electrical activation in all dogs showed consistent slow RV-to-LV propagation of epicardial wave reflecting LBBB condition (as opposed to normal fast uniform activation mediated by Purkinje fibers). Inter-ventricular wave propagation from RV to LV follows the characteristic U-shaped pattern with activation passing through the apex and lines of conduction blocks as described in endocardial non-contact mapping and non-invasive ECGI. The variable location and size of scar seemed to modify the sequence of activation, location of lines of conduction block as well as the region of latest activation. Dogs 1 to 4 with smaller scar burden have very similar activation, implying that small scar only slightly alters the sequence of activation. However, dog 5 with large LCx territory sub-endocardial scar and dog 6 with 2 scar regions had different activation patterns. Lines of conduction blocks were seen in all animals as reported in LBBB patients and seemed to coincide spatially (parallel/overlapping) with the anterior/inferior grooves. This observation shows slow transseptal conduction hypothesized to be a result of more vertical orientation of the laminar myo-sheets near the grooves. The implications of these lines of block have been investigated in a small clinical patient study using non-contact mapping in CRT candidates showing volumetric CRT response at 3 months in patients with lines of conduction blocks as opposed to patients who had homogeneous endocardial conduction. These studies seem to indicate that the benefit of CRT is more dependent on regional LV activation patterns rather than on total LV activation time.

Figures 16A, 16B, 16C, 16D, 16E:
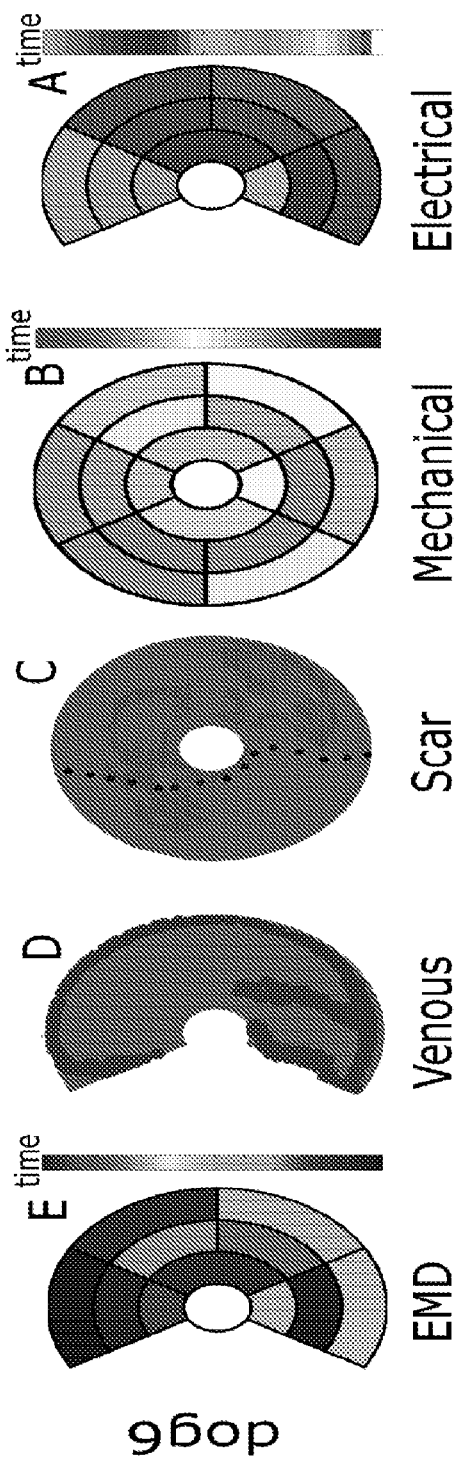
FIGS. 16A-16E illustrate AHA polar plots of all components of the imaging toolbox in dog 6 to facilitate lead implantation planning: epicardial LV electrical activation (FIG. 16A), endocardial LV mechanical activation (FIG. 16B), scar substrate (FIG. 16C), venous tree (FIG. 16D) and EMD maps (FIG. 16E).

FIGS. 16A-16E illustrate AHA polar plots of all components of the imaging toolbox in dog 6 to facilitate lead implantation planning: epicardial LV electrical activation (FIG. 16A), endocardial LV mechanical activation (FIG. 16B), scar substrate (FIG. 16C), venous tree (FIG. 16D) and EMD maps (FIG. 16E).

Figure 17:
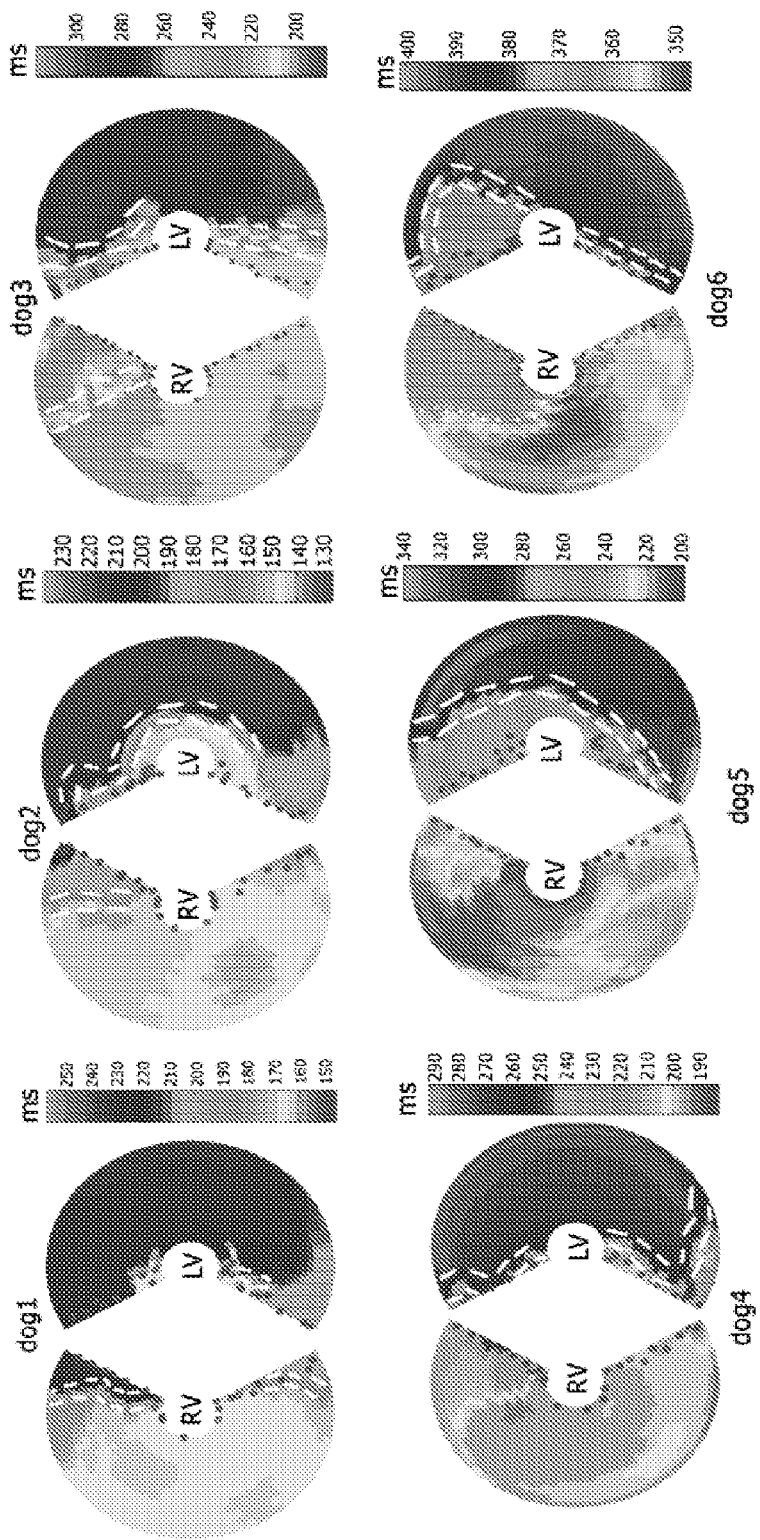
FIG. 17 illustrates regional electrical activation in all animals projected on bullseye plots.
Figure 18:
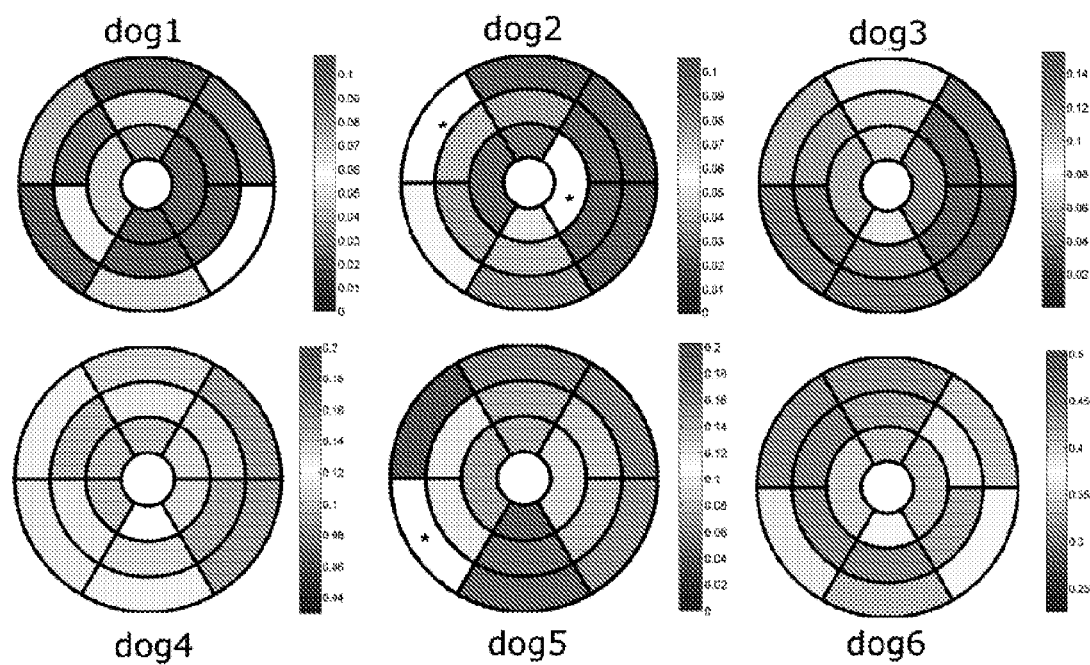
FIG. 18 illustrates regional mechanical activation (time to 10% peak endocardial strain). Star (*) represents akinetic segments not showing distinct large strain peak (<10% median of all strain peaks).
Figure 19:
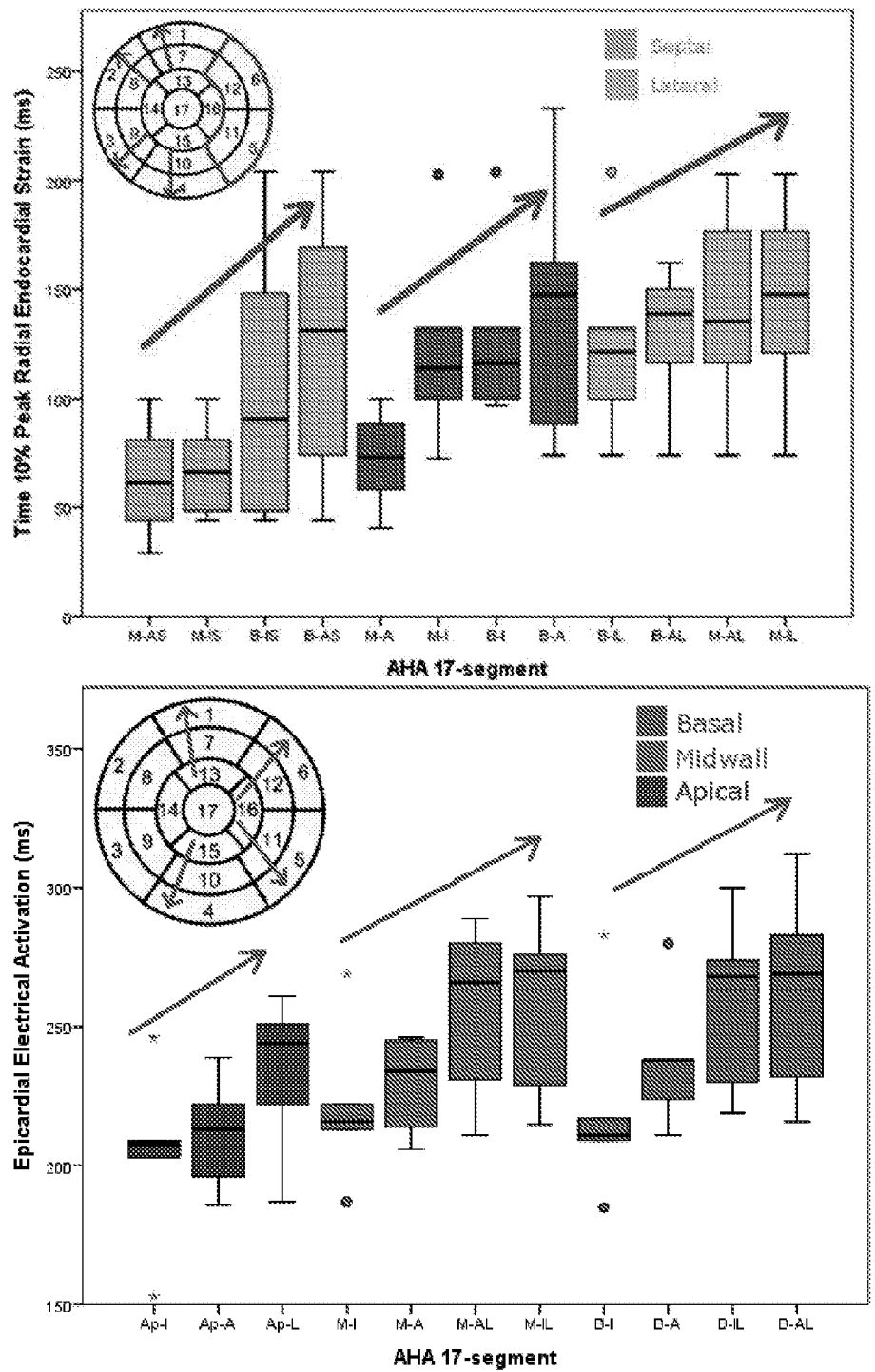
FIG. 19 illustrates time to 10% radial endocardial mechanical activation (septal to lateral—top) and electrical activation (apical to basal—bottom).
Figure 20:
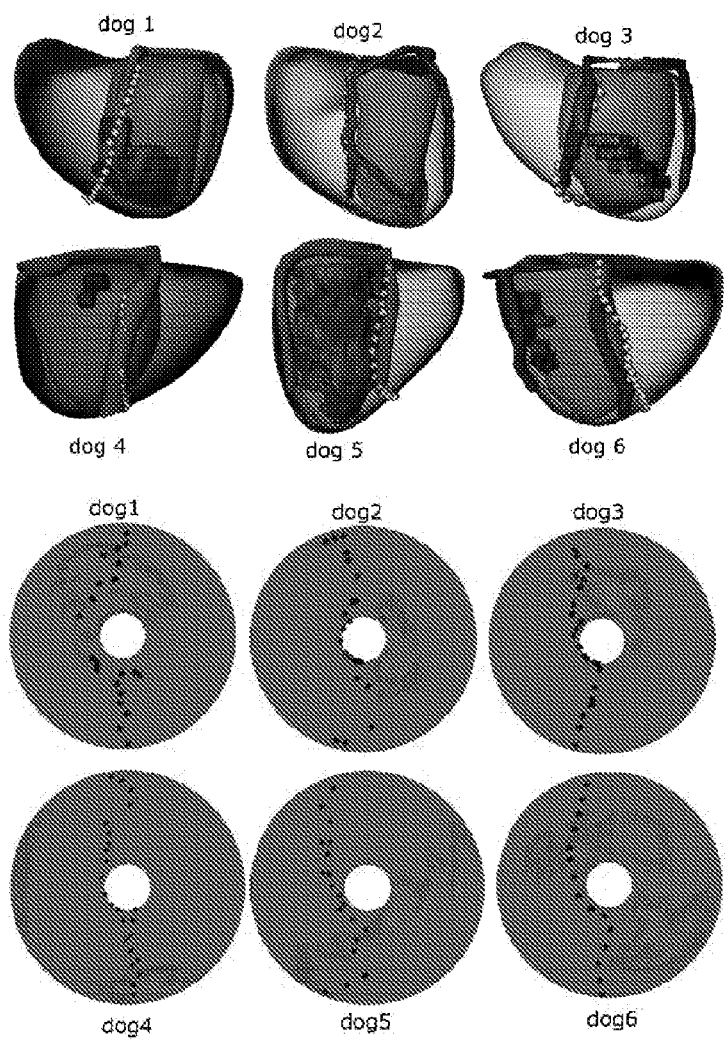
FIG. 20 illustrates three-dimensional and polar projection of endocardial (rather than transmural) extent of infarct.
Figure 21:
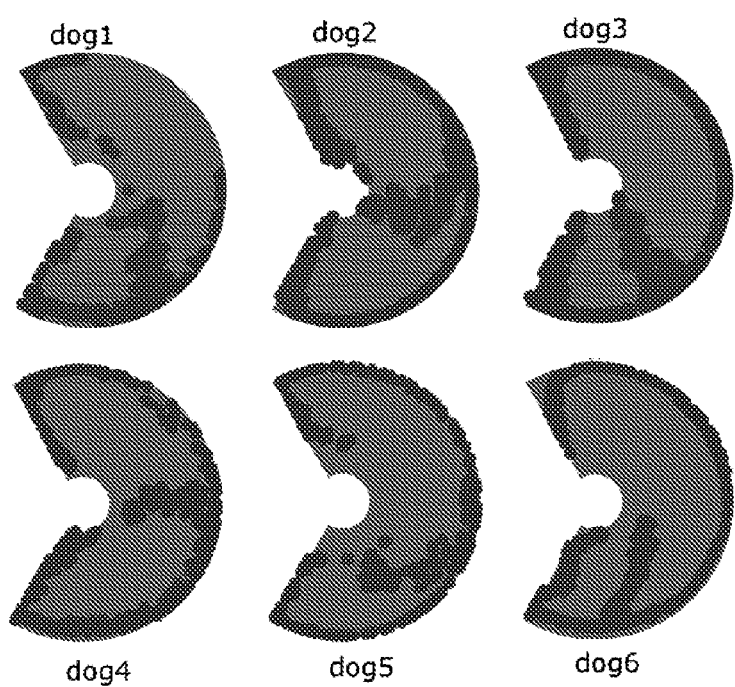
FIG. 21 illustrates polar plots of coronary venous segmented from CT in all animals.

To further describe the exemplary implementation of the present invention, FIG. 17 illustrates regional electrical activation in all animals projected on bullseye plots. FIG. 18 illustrates regional mechanical activation (time to 10% peak endocardial strain). Star (*) represents akinetic segments not showing distinct large strain peak (<10% median of all strain peaks). FIG. 19 illustrates time to 10% radial endocardial mechanical activation (septal to lateral—top) and electrical activation (apical to basal—bottom). M-, mid-wall, B-, basal, -A, anterior, -AL, anterolateral, -AS, anteroseptal, -I, inferior, -IL, inferolateral, -IA, inferoseptal, Ap-, apical. FIG. 20 illustrates three-dimensional and polar projection of endocardial (rather than transmural) extent of infarct. FIG. 21 illustrates polar plots of coronary venous segmented from CT in all animals.

Mechanical Function:

Although the underlying patho-physiological mechanisms of how LBBB induces LV dysfunction remain to be clarified, LBBB yields a disturbance of mechanical coordination between the different regions of the LV walls, especially between septum and lateral wall. Regional mechanical activation sequence derived from radial endocardial strain (time-to-10%-peak) showed general septal to lateral spread with significantly depressed peak percentage thickening in infarcted segments. Pre-stretch was possible to quantify and was shown to be elevated in late-activated lateral regions compared to early-activated septal regions in agreement with clinical and experimental studies.

Scar Substrate and Venous AnatomyTarget Pacing:

The spatial extent of acute and healed myocardial infarction can be quantified accurately with DECT and correlates with delayed-enhancement MR and post-mortem pathology. It is especially important in the context of CRT delivery to map the extent of non-conductive scar as pacing near scar can compromise conduction, increase risk for sudden cardiac death and pump failure in patients and decrease efficacy of pacing compared to pacing remote from scar.

EM Coupling and Delay:

In the normal heart, mechanical activation closely follows electrical activation resulting in homogeneous synchronous contraction. Excitation-contraction coupling in the dyssynchronous failing heart is compromised due to perturbations to cycling of intracellular calcium. This perturbation was shown to manifest as a prolonged EMD between upstroke of action potential and onset of fiber shortening. EMD was shown to have heterogeneous distribution regionally and transmurally dependent on electrical activation, mechanical interactions between myofibers as well as loading conditions of the heart. The exemplary implementation of the present invention confirms heterogeneity of EMD over regional LV segments and a trend of EMD to be prolonged on late-activated segments LV (inferior and posterior).

Clinical Implications:

The conventional approach to CRT has been to place the LV lead in the lateral and posterior wall based on the benefit shown in early hemodynamic studies and the observation that delayed segments predominate at these sites. However, recent data support a more individualized approach to LV lead placement with significant variation in the optimal LV lead position. The imaging toolbox described in this study has the potential to guide device implantation by providing a comprehensive assessment of the electromechanical function, scar substrate and venous structures. For example, in dog 6 (FIG. 6), electrical activation reaches the basal anterolateral wall the latest preceded by the infero-lateral wall. The mechanical activation is broadly late on the lateral wall with infero-lateral segments activating the latest. EMD maps show inferior segments to have the largest delay. Infarcted myocardium is located mid-wall in the apical anterior segment, away from regions of interest on the lateral wall. Synthesizing this information with the venous map can help the implanting clinician optimize pacing location and vein branch to access (e.g., left marginal vein with a mid-wall infero-lateral branch).

The individual EMD maps will be useful in selecting CRT candidates on the premise that patients with highly variable EMD may respond poorly to CRT. Furthermore, EMD maps will likely assist in choosing appropriate sites for LV lead placement, since abnormally prolonged EMD likely represents advanced electro-mechanical disease where pacing may be less effective, and thus should be avoided. These clinical hypotheses are obviously speculative, and are currently being tested in an ongoing clinical investigation.

In the current exemplary implemetion, radiation exposure or iodine contrast dose was not optimized. It is well within possibility of current clinically used imaging protocols to acquire CT images (delayed enhancement and function) in one session with an acceptable radiation dose (about 5 mSv) and contrast dose (about 40 g of iodine). Electro-mechanical delay patterns were not acquired in healthy dogs and values and distribution in normal myocardial segments would further support observations in the current study. Post-CRT follow-up imaging of animals was not performed. Strain was indirectly derived from displacement tracking of endocardial features in dynamic CT images. Infarct size was generally smaller and non-transmural due to the choice of non-permanent occlusion MI model in order to avoid an open-chest procedure which affects the electrical impedance of the chest. Although the sample size in this study is admittedly small, the imaging toolbox is readily applicable to human patients. Inter- and intra-observer variability was not assessed however the methodology is in many aspects quantitative and observer bias will only play a minor role in contouring of DECT images. Further studies are needed to ascertain observations and metrics in a larger human population.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method for optimizing cardiac resynchronization therapy (CRT) comprising:
    receiving, by one or more processors, electrical image data regarding heart function;
    performing, by the one or more processors, calculations using the electrical image data to determine electrical-based heart metrics;
    receiving, by the one or more processors, mechanical image data regarding heart function using computed tomography (CT) scanning,
    the mechanical image data including:
        a series of CT images capturing mechanical contraction,
        images of venous anatomy,
        images of scar regions, and
        images related to blood volume;
    performing, by the one or more processors, calculations using the mechanical image data to determine stretch quantifier of endocardial engraved zones (SQUEEZ) maps at phases of mechanical contraction from end diastole to end systole;

determining, by the one or more processors and based on the electrical-based heart metrics, the mechanical image data, and the SQUEEZ maps, electrical and mechanical activation differences in heart regions other than excluded scar regions to generate an electromechanical delay (EMD) map to select target regions for CRT, wherein the excluded scar regions comprise:
one or more of the scar regions that satisfy a threshold scar value and that are excluded when the electrical and mechanical activation differences are determined; and outputting, by the one or more processors and based on the EMD map, a visual representation of the target regions and a visual representation of the venous anatomy,
the target regions being a first subset of regions of the EMD map having lower electromechanical delays than a second subset of regions of the EMD map.

2. The method of claim 1, wherein receiving the electrical image data comprises:
receiving the electrical image data using body surface potential mapping.

3. The method of claim 1, wherein the electrical-based heart metrics include metrics associated with at least one of:
electrical reconstruction, or
electrical dyssynchrony.

4. The method of claim 1, wherein the electrical-based heart metrics include electrical dyssynchrony metrics associated with at least one of:
a normalized inter-ventricular QRS integral,
a mean total activation,
a normalized inter ventricular QRS integral dispersion,
a dispersion of left ventricle (LV) activation,
a change in QRST integral, or
a uniformity of electrical activation.

5. The method of claim 1, further comprising:
selecting cardiac segments for implantation of epicardial pacing leads.

6. The method of claim 1, further comprising:
selecting routes for implantation of epicardial pacing leads.

7. The method of claim 1, wherein the visual representation of the target regions and the visual representation of the venous anatomy identify heart function.

8. The method of claim 1, further comprising:
processing the electrical image data using dynamic beat-averaging to improve signal-to-noise ratio of the electrical image data.

9. The method of claim 1, further comprising:
filtering the electrical image data digitally in two directions to produce zero-phase shift.

10. The method of claim 1, further comprising:
creating models of heart function using the mechanical image data.

11. The method of claim 1, where determining the electrical and mechanical activation differences comprises:
determining the electrical and mechanical activation differences based on myocardial tissue tracking (MTT).

12. A system for optimizing cardiac resynchronization therapy (CRT) comprising:
one or more processors to:
receive electrical image data regarding heart function;
receive mechanical image data regarding heart function using computed tomography (CT) scanning,
the mechanical image data including:
a series of CT images capturing mechanical contraction,
images of venous anatomy,
images of scar regions, and
images related to blood volume;
perform calculations using the electrical image data to determine electrical-based heart metrics;
perform calculations using the mechanical image data to determine stretch quantifier of endocardial engraved zones (SQUEEZ) maps at phases of mechanical contraction from end diastole to end systole;
determine, based on the electrical-based heart metrics, the mechanical image data, and the SQUEEZ maps, electrical and mechanical activation differences in heart regions other than excluded scar regions to generate an electromechanical delay (EMD) map for selecting target regions for CRT,
wherein the excluded scar regions comprise:
one or more of the scar regions that satisfy a threshold scar value and that are excluded when the electrical and mechanical activation differences are determined; and
output, based on the EMD map, a visual representation of the target regions and a visual representation of the venous anatomy,
the target regions being a first subset of regions of the EMD map having lower electromechanical delays than a second subset of regions of the EMD map.

13. The system of claim 12, wherein the one or more processors, when receiving the electrical image data, are to:
receive the electrical image data using body surface potential mapping.

14. The system of claim 12, wherein the electrical-based heart metrics include metrics associated with at least one of:
electrical reconstruction, or
electrical dyssynchrony.

15. The system of claim 12, wherein the electrical-based heart metrics include electrical dyssynchrony metrics associated with at least one of:
a normalized inter-ventricular QRS integral,
a mean total activation,
a normalized inter ventricular QRS integral dispersion,
a dispersion of left ventricle (LV) activation,
a change in QRST integral, or
a uniformity of electrical activation.

16. The system of claim 12, wherein the one or more processors, when receiving the electrical image data, are to:
receive the electrical image data from surface electrodes.

17. The system of claim 12, wherein the one or more processors are further configured to:
create models of heart function using the mechanical image data.

18. The system of claim 12, wherein the one or more processors, when determining the electrical and mechanical activation differences, are to:
determine the electrical and mechanical activation differences based on myocardial tissue tracking (MTT).

19. A non-transitory computer-readable medium storing instructions, the instructions comprising:
one or more instructions that, when executed by one or more processors, cause the one or more processors to:
receive electrical image data regarding heart function;
receive mechanical image data regarding heart function using computed tomography (CT) scanning, the mechanical image data including:
   a series of CT images capturing mechanical contraction,
   images of venous anatomy,
   images of scar regions, and
   images related to blood volume;
perform calculations using the electrical image data to determine electrical-based heart metrics;
perform calculations using the mechanical image data to determine stretch quantifier of endocardial engraved zones (SQUEEZ) maps at phases of mechanical contraction from end diastole to end systole;
determine, based on the electrical-based heart metrics, the mechanical image data, and the SQUEEZ maps, electrical and mechanical activation differences in heart regions other than excluded scar regions to generate an electromechanical delay (EMD) map for selecting target regions for CRT,
   wherein the excluded scar regions comprise:
      one or more of the scar regions that satisfy a threshold scar value and that are excluded when the electrical and mechanical activation differences are determined; and
   output, based on the EMD map, a visual representation of the target regions and a visual representation of the venous anatomy,
      the target regions being a first subset of regions of the EMD map having lower electromechanical delays than a second subset of regions of the EMD map.

20. The non-transitory computer-readable medium of claim 19, wherein the one or more instructions, when executed by the one or more processors, further cause the one or more processors to:
   create models of heart function using the mechanical image data.

* * * * *